United States Patent
Stillger et al.

(10) Patent No.: US 11,952,602 B2
(45) Date of Patent: Apr. 9, 2024

(54) VARIANTS OF PORCINE TRYPSIN

(71) Applicant: SANOFI-AVENTIS DEUTSCHLAND GMBH, Frankfurt am Main (DE)

(72) Inventors: Thomas Stillger, Frankfurt am Main (DE); Sebastian Rissom, Frankfurt am Main (DE); Claudia Feller, Leipzig (DE); Andreas Vogel, Leipzig (DE)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 0 days.

(21) Appl. No.: 18/050,446

(22) Filed: Oct. 27, 2022

(65) Prior Publication Data
US 2023/0303994 A1 Sep. 28, 2023

Related U.S. Application Data

(62) Division of application No. 16/971,491, filed as application No. PCT/EP2019/054400 on Feb. 22, 2019, now Pat. No. 11,518,988.

(30) Foreign Application Priority Data
Feb. 22, 2018 (EP) .................................... 18158034

(51) Int. Cl.
*C12N 9/76* (2006.01)
*C12N 15/63* (2006.01)

(52) U.S. Cl.
CPC ............ *C12N 9/6427* (2013.01); *C12N 15/63* (2013.01); *C12Y 304/21004* (2013.01)

(58) Field of Classification Search
CPC ................................................... C12N 9/6427
See application file for complete search history.

(56) References Cited

U.S. PATENT DOCUMENTS

| | | |
|---|---|---|
| 7,981,635 B2 | 7/2011 | Zocher et al. |
| 11,518,988 B2 | 12/2022 | Stillger |
| 2020/0377873 A1 | 12/2020 | Stillger |

FOREIGN PATENT DOCUMENTS

| | | |
|---|---|---|
| JP | 2009-507500 A | 2/2009 |
| WO | WO 2007/031187 A1 | 3/2007 |

OTHER PUBLICATIONS uniprot.org, Cationic trypsinogen [Rattus norvegicus], GenBank Accession No. EDM15437.1, Jul. 26, 2016.
uniprot.org, G3V7Q8_RAT, GenBank Accession No. G3V7Q8, Nov. 16, 2011.
Database UNIPROTKB, "Cationic Trypsin-3", Retrieved from EBI, Database Accession No. A0A1S3FKE6, Apr. 12, 2017.
Database UNIPROTKB, "Cationic Trypsinogen", Retrieved from EBI, Database Accession No. G3V7Q8-G3V7Q8_RAT, Nov. 16, 2011.
(Continued)

*Primary Examiner* — Yong D Pak
(74) *Attorney, Agent, or Firm* — LATHROP GPM LLP; James H. Velema, Esq.; Judith L. Stone-Hulslander

(57) ABSTRACT

The present invention relates to polypeptide variants of porcine trypsin, to nucleic acid molecules encoding these variants, and to host cells comprising such nucleic acid molecules. It also relates to the use of these variants in methods for producing insulin. The invention further relates to the use of these variants as medicaments, as food ingredients, or as feed ingredients and to the use of these variants within a process of manufacturing a food ingredient or a feed ingredient.

20 Claims, 4 Drawing Sheets

Specification includes a Sequence Listing.

(56) References Cited

OTHER PUBLICATIONS

International Preliminary Report on Patentability for PCT Application No. PCT/EP2019/054400, dated Aug. 27, 2020, 8 pages.
International Search Report and Written Opinion for PCT Application No. PCT/EP2019/054400, dated Jul. 16, 2019, 14 pages.
Needleman, et al., "A General Method Applicable to the Search for Similarities in the Amino Acid Sequence of Two Proteins", Journal of Molecular Biology, Mar. 1970, vol. 48, No. 3, pp. 443-453.
Pearson, et al., "Improved Tools for Biological Sequence Comparison", Proceedings of the National Academy of the Science of the United States of America, Apr. 1988, vol. 85, No. 8, pp. 2444-2448.
Smith, et al., "Comparison of Biosequences", Advances in Applied Mathematics, Dec. 1981, vol. 2, No. 4, pp. 482-489.
Studier, "Protein Production by Auto-Induction in High-Density Shaking Cultures", Protein Expression and Purification, 2005, vol. 41, No. 1, pp. 207-234.
U.S. Appl. No. 16/971,491, filed Aug. 20, 2020, Thomas Stillger, Variants of Porcine Trypsin.

VARIANTS OF PORCINE TRYPSIN

RELATED APPLICATIONS

This application is a division of U.S. patent application Ser. No. 16/971,491, filed Aug. 20, 2020, which is a 35 U.S.C. § 371 filing of International Patent Application No. PCT/EP2019/054400, filed Feb. 22, 2019, which claims priority to European Patent Application No. 18158034.1, filed Feb. 22, 2018, the entire disclosures of which are hereby incorporated herein by reference.

SEQUENCE LISTING

The instant application contains a Sequence Listing which has been submitted electronically in XML format and is hereby incorporated by reference in its entirety. Said XML copy, created on Mar. 31, 2023, is named 735159_SA9-301USDIV_ST26.xml and is 200,182 bytes in size.

TECHNICAL FIELD OF THE INVENTION

The present invention relates to polypeptide variants of porcine trypsin, to nucleic acid molecules encoding these variants, and to host cells comprising such nucleic acid molecules. It also relates to the use of these variants in methods for producing insulin. The invention further relates to the use of these variants as medicaments, as food ingredients, or as feed ingredients and to the use of these variants within a process of manufacturing a food ingredient or a feed ingredient.

BACKGROUND OF THE INVENTION

The endopeptidase trypsin is used for the manufacture of human insulin, insulin analogues and also for insulin derivatives. The human insulin, the insulin analogue, or the insulin derivative is generated from a pre-pro insulin (PPI) by enzymatic hydrolysis using trypsin, wherein the pre-sequence and the C-peptide are cleaved off in order to yield the respective products (see FIG. 1). Trypsin is specific to cleave at the C-terminal side of Arg and Lys residues within the polypeptide chain. Within the pre-pro human insulin and pre-pro insulin glargine polypeptide, several Arg and Lys residues are present, including B29Lys, B31Arg, and B32Arg at the junction of B chain and C peptide. Therefore, pre-pro human insulin and pre-pro insulin glargine are cleaved by trypsin at the C-terminal side of Arg and Lys residues, including at the C-terminal side of B29Lys, and B31Arg and B32Arg. For the manufacturing of insulin glargine, the trypsin cleavage after B32Arg provides the final insulin glargine. Trypsin cleavage after B29Lys and B31Arg leads to by-products desB30-Thr ("des-Thr")-insulin glargine and desB32Arg-insulin glargine (also referred to as "des-Arg"). Therefore, it is required to remove the by-products in the manufacturing process of insulin glargine.

For the manufacturing of human insulin, the trypsin cleavage after B31Arg leads to B31Arg-human insulin (also referred to as "mono-Arg") and after B32Arg to B31Arg-B32Arg-human insulin (also referred to as "di-Arg"). Both are intermediates in said manufacturing process. In the subsequent manufacturing process, these two intermediates are both converted to the final human insulin. Trypsin cleavage after B29Lys leads to by-product desB30-Thr ("des-Thr")-human insulin. Therefore, it is required to remove the by-product in the manufacturing process of human insulin.

For the manufacturing of human insulin and insulin glargine, a trypsin cleavage after B32Arg leads to the final insulin glargine and for human insulin it leads to an intermediate which is converted to the final human insulin in subsequent process steps.

To address the undesired formation of a desB30-Thr-intermediate, past development has led to a porcine trypsin variant S172A that reduces this mis-cleavage via an increase of selectivity towards the C-terminal side of Arg versus Lys. Porcine trypsin variant S172A is described in international patent application WO 2007/031187 A1, which is hereby incorporated by reference in its entirety.

Now, when the inventors carefully observed the kinetics of the trypsin S172A catalysed reaction, they surprisingly found out that the formation of miss-cleaved by-products would not only be due to a primary miss-cleavage of the PPI by trypsin acting as an endo-protease such as described in the literature, but also by a side-activity intrinsic to porcine trypsin as well as its variant S172A acting as an exopeptidase. The exopeptidase activity leads to degradation of insulin glargine under formation of des-Arg and des-Thr also.

Technical Problems Underlying the Present Invention

Thus, there was a need in the prior art for novel trypsin variants with reduced side-activities, especially with a reduced exo-peptidase activity. Such novel trypsin variants will reduce the amount of by-products in the cleavage of PPI and will lead to higher yields of insulin and insulin derivatives when producing insulin (or insulin derivatives) from PPI.

The inventors have prepared novel variants of porcine trypsin that have a reduced exopeptidase activity and/or that show a reduced formation of by-products in the PPI cleavage reaction.

The above overview does not necessarily describe all problems solved by the present invention.

SUMMARY OF THE INVENTION

In a first aspect, the present invention relates to a variant of porcine trypsin comprising or consisting of an amino acid sequence that has at least 90% sequence identity to SEQ ID NO: 1, wherein said amino acid sequence differs from SEQ ID NO: 1 at least by one or more amino acid substitutions at one or more positions corresponding to F24, S44, D56, G78, Y131, S172 and W193 of native porcine trypsin according to SEQ ID NO: 1,
with the proviso that said amino acid sequence is not native porcine trypsin according to SEQ ID NO: 1; and
with the proviso that said amino acid sequence is not porcine variant trypsin S172A according to SEQ ID NO: 2.

In a second aspect, the present invention relates to a nucleic acid molecule encoding a variant of porcine trypsin according to the first aspect.

In a third aspect, the present invention relates to a host cell containing a nucleic acid molecule according to the second aspect.

In a fourth aspect, the present invention relates to a method of producing a variant of porcine trypsin according to the first aspect comprising the step of:

cultivating a host cell according to the third aspect and isolating the variant of porcine trypsin from the culture medium or from the host cell.

In a fifth aspect, the present invention relates to a variant of porcine trypsin according to the first aspect or a nucleic acid molecule according to the second aspect or a host cell according to the third aspect for use as a medicament; for use as a food ingredient; for use as a feed ingredient or for use within a process of manufacturing a food ingredient or a feed ingredient.

In a sixth aspect, the present invention relates to a use of the variant of porcine trypsin according to the first aspect in a method for the production of human insulin, an insulin analogue or a derivative of insulin.

In a seventh aspect, the present invention relates to a use of the variant of porcine trypsin according to the first aspect to cleave a protein or peptide with the general formula A-Lys-Thr-Arg-Arg-B (SEQ ID NO: 131),
wherein A is an amino acid sequence consisting of one or more amino acids; and
wherein B is an amino acid sequence consisting of one or more amino acids.

In an eighth aspect, the present invention relates to a composition comprising a variant of porcine trypsin according to the first aspect or a nucleic acid molecule according to the second aspect or a host cell according to the third aspect.

DETAILED DESCRIPTION OF THE INVENTION

Definitions

Figure 1:
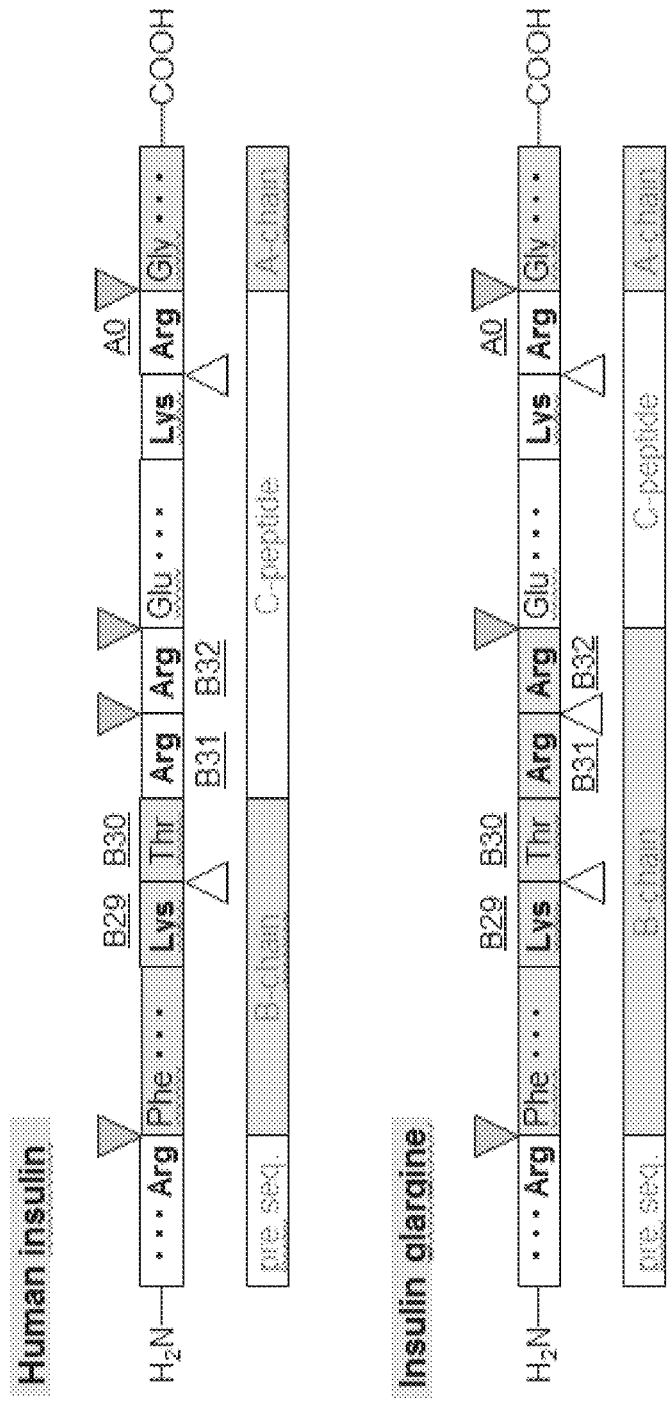
FIG. 1 shows the scheme of main tryptic cleavage sites for the pro-pro-insulins of human insulin and insulin glargine. Filled triangles denote cleavage sites yielding product(s), open triangles denote cleavage sites yielding by-products. The disulfide bonds of the pre-pre-insulins are not displayed.

Although the present invention is described in detail below, it is to be understood that this invention is not limited to the particular methodologies, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art to which this invention belongs.

The practice of the present invention will employ, unless otherwise indicated, conventional methods of chemistry, biochemistry, cell biology, immunology, and recombinant DNA techniques which are explained in the literature in the field.

Throughout this specification and the claims which follow, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps, although in some embodiments such other member, integer or step or group of members, integers or steps may be excluded, i.e. the subject-matter consists in the inclusion of a stated member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as"), provided herein is intended merely to better illustrate the invention and does not pose a limitation on the scope of the invention otherwise claimed. No language in the specification should be construed as indicating any non-claimed element essential to the practice of the invention.

Several documents (for example: patents, patent applications, scientific publications, manufacturers specifications, instructions, GenBank Accession Number sequence submissions etc.) are cited throughout the text of this specification. Nothing herein is to be construed as an admission that the invention is not entitled to antedate such disclosure by virtue of prior invention. Some of the documents cited herein are characterized as being "incorporated by reference" or "incorporated by reference in their entirety". In the event of a conflict between the definitions or teachings of such incorporated references and definitions or teachings recited in the present specification, the text of the present specification takes precedence.

Sequences: All sequences referred to herein are disclosed in the attached sequence listing that, with its whole content and disclosure, is a part of this specification.

The term "naturally occurring" when used in connection with biological materials, such as nucleic acid molecules, (poly-)peptides, host cells, and the like, refers to materials which are found in nature and are not manipulated by man.

The term "amino acid" or "amino acid residue", as used herein, refers to naturally occurring amino acids, unnatural amino acids, amino acid analogues and amino acid mimetics that function in a manner similar to the naturally occurring amino acids, all in their D and L stereoisomers if their structure allows such stereoisomeric forms. Amino acids are referred to herein by either their name, their commonly known three letter symbols or by the one-letter symbols recommended by the IUPAC-IUB Biochemical Nomenclature Commission.

When used in connection with amino acids, the term "naturally occurring" refers to the 20 conventional amino acids (i.e., alanine (A), cysteine (C), aspartic acid (D), glutamic acid (E), phenylalanine (F), glycine (G), histidine (H), isoleucine (I), lysine (K), leucine (L), methionine (M), asparagine (N), proline (P), glutamine (Q), arginine (R), serine (S), threonine (T), valine (V), tryptophan (W), and tyrosine (Y)), as well as selenocysteine, pyrrolysine (PYL), and pyrroline-carboxylysine (PCL). The terms "naturally occurring amino acids" and "codable amino acids" are used interchangeably herein.

The term "unnatural amino acid", as used herein, is meant to refer to amino acids that are not naturally encoded or found in the genetic code of any organism.

The term "amino acid analogue", as used herein, refers to compounds that have the same basic chemical structure as a naturally occurring amino acid.

The term "amino acid mimetics", as used herein, refers to chemical compounds that have a structure that is different from the general chemical structure of an amino acid, but functions in a manner similar to a naturally occurring amino acid.

The term "peptide", as used herein, refers to a polymeric form of amino acids of any length, for example, comprising two or more, or 3 or more, or 4 or more, or 6 or more, or 8 or more, or 9 or more, or 10 or more, or 13 or more, or 16 or more, or 21 or more amino acids joined covalently by peptide bonds. The term "polypeptide" refers to large peptides, in particular to peptides with more than 100 amino acid residues. The terms "polypeptide" and "protein" are used interchangeably herein. The present application provides amino acid sequence information for several peptides and polypeptides disclosed herein. The amino acid sequences are presented herein from the amino terminus (on the left) to the carboxy terminus (on the right) of the peptide or polypeptide.

As used herein, a "variant" of a (poly)peptide refers to a (poly)peptide that differs from a corresponding reference (poly)peptide by one or more amino acid modifications in its amino acid sequence. In one embodiment, the "variant" maintains one or more biological activities of the reference (poly)peptide. The reference (poly)peptide can be a wild-type (poly)peptide or a (poly)peptide that is not naturally occurring. The term "variant" and "mutant" are used interchangeably herein.

As used herein, the term "variant of porcine trypsin" refers to a polypeptide that differs from wild-type porcine trypsin as shown in SEQ ID NO: 1 by one or more amino acid modifications in its amino acid sequence. The term "variant of porcine trypsin" particularly refers to a polypeptide that differs from wild-type porcine trypsin as shown in SEQ ID NO: 1 by one or more amino acid exchanges. According to the present invention, a "variant of porcine trypsin" exhibits an endoproteolytic activity similar to the endoproteolytic activity of a reference trypsin (e.g. wild-type porcine trypsin according to SEQ ID NO: 1 or trypsin variant S172A according to SEQ ID NO: 2) but the endo-proteolytic activities of the "variant of porcine trypsin" and the reference trypsin can differ in their selectivity for certain cleavage sites.

The term "amino acid modifications" encompasses amino acid exchanges, amino acid deletions, and amino acid additions. The terms "amino acid exchange" and "amino acid substitution" are used interchangeably herein. The term "amino acid deletions" encompasses N-terminal truncations, internal deletions, and C-terminal truncations. The term "amino acid additions" encompasses N-terminal additions, amino acid insertions, and C-terminal additions.

The expression "Xaa24" (and similar expressions, such as Xaa44, Xaa56, Xaa78, etc.) refers to a variable amino acid at position 24 (or 44, 56, 78, etc., respectively) of a given amino acid sequence. The sequence listing furnished with the present application contains one protein sequence with variable amino acid positions, namely SEQ ID NO: 3. The variable amino acid postions within the protein sequence according to SEQ ID NO: 3 are indicated by the amino acid Xaa (in three-letter code format). The number 24 in this example indicates that this variable position is the 24th amino acid of the protein sequence according to SEQ ID NO: 3. Likewise, the expression Xaa44 indicates that the 44th position of SEQ ID NO: 3 is a variable amino acid position, and so forth.

As used herein, the term "human insulin" refers to the human hormone whose structure and properties are well-known. Human insulin has two peptide chains (chains A and B) that are connected by disulphide bridges between cysteine residues, namely the A-chain and the B-chain. The A-chain is a 21 amino acid peptide and the B-chain is a 30 amino acid peptide, the two chains being connected by three disulphide bridges: one between the cysteines in position 6 and 11 of the A-chain; the second between the cysteine in position 7 of the A-chain and the cysteine in position 7 of the B-chain; and the third between the cysteine in position 20 of the A-chain and the cysteine in position 19 of the B-chain.

As used herein, the terms "derivative of insulin" and "insulin derivative" refer to a peptide which has a molecular structure which formally can be derived from the structure of a naturally occurring insulin, for example that of human insulin, in which one or more organic substituents (e.g. a fatty acid) is bound to one or more of the amino acids. Optionally, one or more amino acids occurring in the naturally occurring insulin may have been deleted and/or replaced by other amino acids, including non-codable amino acids, or amino acids, including non-codable, have been added to the naturally occurring insulin. Examples of derivatives of insulin include, but are not limited to, the following:

(i). 'Insulin detemir' which differs from human insulin in that the C-terminal threonine in position B30 is removed and a fatty acid residue (myristic acid residue) is attached to the epsilon-amino function of the lysine in position B29.

(ii). 'Insulin degludec' which differs from human insulin in that the last amino acid is deleted from the B-chain and by the addition of a glutamyl link from B29Lys to a hexadecanedioic acid.

As used herein, the terms "analogue of insulin" and "insulin analogue" refer to a peptide which has a molecular structure which formally can be derived from the structure of a naturally occurring insulin, for example that of human insulin, by deleting and/or exchanging at least one amino acid residue occurring in the naturally occurring insulin and/or adding at least one amino acid residue. The added and/or exchanged amino acid residue can either be a codable amino acid residue or another naturally occurring residue or a purely synthetic amino acid residue. Examples of analogues of insulin include, but are not limited to, the following:

(i). 'Insulin aspart' is created through recombinant DNA technology so that the amino acid B28 in human insulin (i.e. the amino acid no. 28 in the B chain of human insulin), which is proline, is replaced by aspartic acid;

(ii). 'Insulin lispro' is created through recombinant DNA technology so that the penultimate lysine and proline residues on the C-terminal end of the B-chain of human insulin are reversed (human insulin: B28Pro-B29Lys; insulin lispro: B28Lys-B29Pro);

(iii). 'Insulin glulisine' differs from human insulin in that the amino acid asparagine at position B3 is replaced by lysine and the lysine in position B29 is replaced by glutamic acid;

(iv). 'Insulin glargine' differs from human insulin in that the asparagine at position A21 is replaced by glycine and the B chain is extended at the carboxy terminal by two arginines.

As used herein, the term "yield" refers to the ratio of the resulting product (i.e insulin or insulin derivative or insulin analogue) obtained after the trypsin cleavage and the pre-pro insulin (or pre-pro-insulin derivative or pre-pro-insulin analogue) before trypsin cleavage. The yield depends on the selectivity of the trypsin variant to cleave at the desired cleavage site and on its exonuclease activity. The higher the selectivity of the trypsin variant to cleave at the desired cleavage site only and the lower its exonuclease activity, the higher the yield.

For example, "yield of insulin glargine" or "yield of B31Arg-B32Arg-human insulin" refer to the ratio of the resulting insulin glargine or the B31Arg-B32Arg-human insulin obtained after the trypsin cleavage and the pre-pro insulin glargine or human pre-pro-insulin, respectively, before trypsin cleavage. The "yield of insulin glargine" and the "yield of B31Arg-B32Arg-human insulin" depend on the selectivity of the trypsin variant to cleave after B32Arg only and on its exonuclease activity. The higher the selectivity of the trypsin variant to cleave after B32Arg only and the lower its exonuclease activity, the higher the yield.

As used herein, the term "increased selectivity" refers to the property of a trypsin variant to cleave to a lesser extent at an undesired cleavage site and to a higher extent at the desired cleavage site as compared to a reference trypsin. An increased selectivity results in a reduced formation of undesired by-products. The reference trypsin can be for example, wild-type porcine trypsin according to SEQ ID NO: 1 or trypsin variant S172A according to SEQ ID NO: 2.

"Sequence identity" between two amino acid sequences indicates the percentage of amino acids that are identical between the sequences. The optimal alignment of the sequences for comparison may be produced, besides manually, by means of the local homology algorithm of Smith and Waterman, 1981, Adv. App. Math. 2, 482-489 (herewith incorporated by reference), by means of the local homology algorithm of Needleman and Wunsch, 1970, J. Mol. Biol. 48, 443-453 (herewith incorporated by reference), by means of the similarity search method of Pearson and Lipman, 1988, Proc. Natl Acad. Sci. USA 85, 2444-2448 (herewith incorporated by reference), or by means of computer programs which use these algorithms (GAP, BESTFIT, FASTA, BLAST P, BLAST N and TFASTA in Wisconsin Genetics Software Package, Genetics Computer Group, 575 Science Drive, Madison, Wis.).

In the context of the present invention, the extent of sequence identity between a modified sequence and the sequence from which it is derived is generally calculated with respect to the total length of the unmodified sequence, if not explicitly stated otherwise. In embodiments, where neither sequence is a modified sequence, the extent of sequence identity is calculated with respect to the total length of the sequence defined as reference sequence, unless stated otherwise. In embodiments, where neither sequence can be regarded as a reference sequence, the extent of sequence identity is calculated with respect to the longer of the two sequences, unless stated otherwise.

A "nucleic acid molecule" according to some embodiments of the invention is deoxyribonucleic acid (DNA) or ribonucleic acid (RNA). A nucleic acid molecule according to the invention may be in the form of a molecule which is single-stranded or double-stranded; and may be linear or covalently closed to form a circle.

The term "DNA" relates to a molecule which comprises deoxyribonucleotide residues and which can entirely or substantially be composed of deoxyribonucleotide residues. "Deoxyribonucleotide" relates to a nucleotide which lacks a hydroxyl group at the 2'-position of a beta-D-ribofuranosyl group. The term "DNA" comprises isolated DNA such as partially or completely purified DNA, essentially pure DNA, synthetic DNA, and recombinantly generated DNA and includes modified DNA which differs from naturally occurring DNA by addition, deletion, substitution and/or alteration of one or more nucleotides. Such alterations can include addition of non-nucleotide material, such as to the end(s) of a DNA or internally, for example at one or more nucleotides of the DNA. Nucleotides in DNA molecules can also comprise non-standard nucleotides, such as non-naturally occurring nucleotides or chemically synthesized nucleotides. These altered DNAs can be referred to as analogues or analogues of naturally-occurring DNA. When used in connection with nucleotides, the term "naturally occurring" refers to the bases adenine (A), cytosine (C), guanine (G), thymine (T), and uracil (U).

The term "RNA" relates to a molecule which comprises ribonucleotide residues and which can entirely or substantially be composed of ribonucleotide residues. "Ribonucleotide" relates to a nucleotide with a hydroxyl group at the 2'-position of a beta-D-ribofuranosyl group. The term "RNA" comprises isolated RNA such as partially or completely purified RNA, essentially pure RNA, synthetic RNA, and recombinantly generated RNA and includes modified RNA which differs from naturally occurring RNA by addition, deletion, substitution and/or alteration of one or more nucleotides. Such alterations can include addition of non-nucleotide material, such as to the end(s) of a RNA or internally, for example at one or more nucleotides of the RNA. Nucleotides in RNA molecules can also comprise non-standard nucleotides, such as non-naturally occurring nucleotides or chemically synthesized nucleotides or deoxynucleotides. These altered RNAs can be referred to as analogues or analogues of naturally-occurring RNA. According to the invention, "RNA" refers to single-stranded RNA or double stranded RNA. In one embodiment, the RNA is mRNA, e.g., in vitro transcribed RNA (IVT RNA) or synthetic RNA. The RNA may also be modified, e.g., with one or more modifications increasing the stability (e.g., the half-life) of the RNA. Such modifications are known to a person skilled in the art and include, for example, 5'-caps or 5'cap analogues.

The nucleic acid molecule according to the present invention may be contained/comprised in a vector. The term "vector", as used herein, includes all vectors known to the skilled person, including plasmid vectors, cosmid vectors, phage vectors, such as lambda phage, viral vectors, such as adenoviral or baculoviral vectors, or artificial chromosome vectors such as bacterial artificial chromosomes (BAC), yeast artificial chromosomes (YAC), or P1 artificial chromosomes (PAC). Said vectors include expression as well as cloning vectors. Expression vectors comprise plasmids as well as viral vectors and generally contain a desired coding sequence and appropriate DNA sequences necessary for the expression of the operably linked coding sequence in a particular host organism (e.g., bacteria, yeast, plant, insect, or mammal) or in in vitro expression systems. Cloning vectors are generally used to engineer and amplify a certain desired DNA fragment and may lack functional sequences needed for expression of the desired DNA fragments.

Alternatively, the nucleic acid molecule according to the present invention may be integrated into a genome, e.g., the genome of a host cell. Means and methods to integrate a particular nucleic acid molecule into a genome are known to a person skilled in the art.

The term "cell" or "host cell" generally relates to an intact cell, i.e., a cell with an intact membrane that has not released its normal intracellular components such as enzymes, organelles, or genetic material. An intact cell generally is a viable cell, i.e. a living cell capable of carrying out its normal metabolic functions. As used herein, said term relates to any cell which can be transfected or transformed with an exogenous nucleic acid. In some embodiments, the cell when transfected or transformed with an exogenous nucleic acid and transferred to a recipient can express the nucleic acid in the recipient. The term "cell" includes prokaryotic cells, such as bacterial cells, and eukaryotic cells, such as yeast cells, fungal cells or mammalian cells. Bacterial cells include cells from gram-negative bacterial strains, such as strains of *Escherichia coli, Proteus*, and *Pseudomonas*, and gram-positive bacterial strains, such as strains of *Bacillus, Streptomyces, Staphylococcus*, and *Lactococcus*. Fungal cells include cells from the species of *Trichoderma, Neurospora*, and *Aspergillus*. Yeast cells include cells from the species of *Saccharomyces* (for example, *Saccharomyces cerevisiae*), *Schizosaccharomyces* (for example, *Schizosaccharomyces pombe*), *Pichia* (for example, *Pichia pastoris* and *Pichia methanolica*), *Komagataella* (for example, *Komagataella pastoris* and *Komagataella phaffii*) and *Hansenula*. Mammalian cells include for example CHO cells, BHK cells, HeLa cells, COS cells, HEK293 and the like. Amphibian cells, insect cells, plant cells, and any other cells used in the art for the expression of heterologous proteins can be used as well. Mammalian cells are particularly suitable for adoptive transfer, such as cells from humans, mice, hamsters, pigs, goats, and primates. The cells may be derived from a large number of tissue types and include primary cells and cell lines such as cells of the immune system, in particular antigen-presenting cells such as dendritic cells and T cells, stem cells such as hematopoietic stem cells and mesenchymal stem cells and other cell types. An antigen-presenting cell is a cell that displays antigen in the context of major histocompatibility complex on its surface. T cells may recognize this complex using their T cell receptor (TCR). The "cell" or "host cell" may be isolated or part of a tissue or organism, in particular a "non-human organism".

The term "non-human organism", as used herein, is meant to include non-human primates or other animals, in particular mammals, such as cows, horses, pigs, sheep, goats, dogs, cats, rabbits or rodents, such as mice, rats, guinea pigs and hamsters.

The term "medicament", as used herein, refers to a substance/composition used in therapy, i.e., in the treatment of a disease or disorder.

According to the invention, the term "disease or disorder" refers to any pathological or unhealthy state.

By "treat" is meant to administer a compound or composition or a combination of compounds or compositions to a subject in order to prevent or eliminate a disease or disorder; arrest or slow a disease or disorder in a subject; inhibit or slow the development of a new disease or disorder in a subject; decrease the frequency or severity of symptoms and/or recurrences in a subject who currently has or who previously has had a disease or disorder; and/or prolong, i.e., increase, the lifespan of the subject.

In particular, the term "treating/treatment of a disease or disorder" includes curing, shortening the duration, ameliorating, preventing, slowing down or inhibiting progression or worsening, or preventing or delaying the onset of a disease or disorder or the symptoms thereof.

The term "subject" means according to the invention a subject for treatment, in particular a diseased subject (also referred to as "patient"), including human beings, non-human primates or other animals, in particular mammals, such as cows, horses, pigs, sheep, goats, dogs, cats, rabbits or rodents, such as mice, rats, guinea pigs and hamsters. In one embodiment, the subject/patient is a human being.

A "composition" in accordance with the present invention contains an effective amount of the variant of porcine trypsin of the invention (also referred to herein as "active agent"). The composition in accordance with the present invention may be used (a) in a manufacturing process, in particular in a manufacturing process to prepare peptides, in particular in a manufacturing process to prepare human insulin, insulin derivatives and/or insulin analogues; (b) as food ingredient; (c) as feed ingredient, (d) or for use within a process of manufacturing a food ingredient or a feed ingredient. The composition in accordance with the present invention may also be used for the treatment of a disease of a disorder and so may be a pharmaceutical composition.

A "pharmaceutical composition" in accordance with the present invention contains a therapeutically effective amount of the variant of porcine trypsin, the nucleic acid molecule or the host cell of the invention (also referred to herein as "active agents") to generate the desired reaction or the desired effect. The pharmaceutical composition in accordance with the present invention may further comprise at least one other active agent(s).

In one embodiment, compositions are provided in a uniform dosage form and may be prepared in a manner known per se. A composition may, e.g., be in the form of a solution or suspension.

A composition or a pharmaceutical composition may further comprise one or more excipients. In one embodiment of a pharmaceutical composition, the one or more excipients are all pharmaceutically acceptable. As used herein, "pharmaceutically acceptable" refers to physiologically well-tolerated by a mammal or a human. In particular, it means approved by a regulatory agency of the Federal or a state government or listed in the U.S. Pharmacopeia or other generally recognized pharmacopeia for use in animals, and more particularly in humans.

A composition or a pharmaceutical composition according to the invention may be present in the form of a composition, wherein different active agents and excipients (e.g. diluents and/or carriers) are admixed with each other, or may take the form of a combined preparation, where active agents are present in partially or totally distinct form. An example for such a combination or combined preparation is a kit-of-parts.

If the context does not state otherwise, the terms "active agent" and "active ingredient" refer to the variants of porcine trypsin of the invention, to the nucleic acid molecule of the invention and to the host cell of the invention. The terms "active agent" and "active ingredient" are used interchangeably herein.

The term "carrier" refers to an organic or inorganic component, of a natural or synthetic nature, in which the active agent is combined in order to facilitate, enhance or enable application. According to the invention, the term "carrier" also includes one or more compatible solid or liquid fillers, diluents, adjuvants, excipients, vehicles, or encapsulating substances. Such carriers can be sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition or the pharmaceutical composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition or the pharmaceutical composition can be formulated as a suppository, with traditional binders and carriers such as triglycerides. The compounds of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. Such compositions will contain an effective amount of the compound, in some embodiments in purified form, together with a suitable amount of carrier. The formulation should suit the mode of administration.

The term "excipient", as used herein, is intended to include all substances which may be present in a composition or in a pharmaceutical composition and which are not active agents, such as salts, binders (e.g., lactose, dextrose, sucrose, trehalose, sorbitol, mannitol), carriers, lubricants, thickeners, surface active agents, preservatives (e.g. antioxidants, citric acid, sodium citrate, benzalkonium chloride, chlorobutanol, cysteine, methionine, parabens, thimerosal), emulsifiers, buffer substances, flavouring agents, or colorants.

Salts are included in the invention and may also be pharmaceutically acceptable salts. Salts or pharmaceutically acceptable salts of this kind comprise in a non-limiting way those prepared from the following acids: hydrochloric, hydrobromic, sulfuric, nitric, phosphoric, maleic, acetic, salicylic, citric, formic, malonic, succinic acids, and the like. Salts and pharmaceutically acceptable salts may also be prepared as alkali metal salts or alkaline earth metal salts, such as sodium salts, potassium salts or calcium salts. Salts may be added to adjust the ionic strength or tonicity.

Suitable buffer substances for use in a composition or in a pharmaceutical composition according to the invention include acetic acid in a salt, citric acid in a salt, boric acid in a salt and phosphoric acid in a salt.

The composition or the pharmaceutical composition may also be formulated as a stable lyophilized product that is reconstituted with an appropriate diluent, which, optionally, comprises one or more excipients as defined above.

The active agents and the pharmaceutical compositions described herein can be administered in therapeutically effective amounts. A "therapeutically effective amount" refers to the amount, which achieves a desired therapeutic reaction or a desired therapeutic effect alone or together with further doses, in one embodiment without causing unacceptable side-effects. In the case of treatment of a particular disease or of a particular condition, the desired reaction can relate to inhibition of the course of the disease. This comprises slowing down the progress of the disease and, in particular, interrupting or reversing the progress of the disease. The desired reaction in a treatment of a disease or of a condition may also be delay of the onset or a prevention of the onset of said disease or said condition. An effective amount of an agent or composition described herein will depend on the condition to be treated, the severity of the disease, the individual parameters of the subject (including age, physiological condition, size and weight), the duration of treatment, the type of an accompanying therapy (if present), the specific route of administration and similar factors. Accordingly, the doses administered of the agents described herein may depend on several of such parameters. In the case that a reaction in a subject is insufficient with an initial dose, higher doses (or effectively higher doses achieved by a different, more localized route of administration) may be used.

As used herein, the term "kit of parts (in short: kit)" refers to an article of manufacture comprising one or more containers and, optionally, a data carrier. Said one or more containers may be filled with one or more of the above mentioned (re-)agents. Additional containers may be included in the kit that contain, e.g., diluents, buffers and further reagents. Said data carrier may be a non-electronical data carrier, e.g., a graphical data carrier such as an information leaflet, an information sheet, a bar code or an access code, or an electronical data carrier such as a compact disk (CD), a digital versatile disk (DVD), a microchip or another semiconductor-based electronical data carrier. The access code may allow the access to a database, e.g., an internet database, a centralized, or a decentralized database. Said data carrier may comprise instructions for the use of the active agents of the present invention. For example, the data carrier may comprise instructions for the use of the active agents (a) in a manufacturing process, in particular in a manufacturing process to prepare peptides, in particular in a manufacturing process to prepare human insulin, insulin derivatives and/or insulin analogues; (b) as food ingredient; (c) as feed ingredient, (d) or for use within a process of manufacturing a food ingredient or a feed ingredient.

As used herein, the term "pre-pro insulin" or the abbreviation "PPI" refers to a single chain insulin precursor starting from the N-terminal part with a pre-sequence followed by the B-chain, C-peptide and the A-chain (see FIG. 1).

Embodiments of the Invention

In the following paragraphs, certain elements of the present invention will be described. These elements may be listed with specific embodiments, however, it should be understood that they may be combined in any manner and in any number to create additional embodiments. The variously described examples and embodiments should not be construed to limit the present invention to only the explicitly described embodiments. This description should be understood to support and encompass embodiments which combine the explicitly described embodiments with any number of the disclosed elements. Furthermore, any permutations and combinations of all described elements in this application should be considered disclosed by the description of the present application unless the context indicates otherwise.

In a first aspect, the present invention is directed to a variant of porcine trypsin comprising or consisting of an amino acid sequence that has at least 90% sequence identity to SEQ ID NO: 1, wherein said amino acid sequence differs from SEQ ID NO: 1 at least by one or more amino acid substitutions at one or more positions corresponding to F24, S44, D56, G78, Y131, S172 and W193 of native porcine trypsin according to SEQ ID NO: 1, with the proviso that said amino acid sequence is not native porcine trypsin according to SEQ ID NO: 1; and with the proviso that said amino acid sequence is not porcine variant trypsin S172A according to SEQ ID NO: 2.

In one embodiment of the first aspect,
the amino acid at the position corresponding to F24 is not substituted by Asp, Glu, or Gly;
the amino acid at the position corresponding to S44 is not substituted by Tyr;
the amino acid at the position corresponding to Y131 is not substituted by Lys or Pro;
and/or the amino acid at the position corresponding to W193 is not substituted by Asn or Cys.

In one embodiment of the first aspect,
the amino acid at the position corresponding to F24 is substituted by an amino acid selected from the group consisting of Ala, Asn, Arg, Gln, Ile, Leu, Lys, Met, Ser, Thr, and Val;
the amino acid at the position corresponding to S44 is substituted by an amino acid selected from the group consisting of Leu and Pro;
the amino acid at the position corresponding to D56 is substituted by an amino acid selected from the group consisting of Ala, Asn, His, and Trp;
the amino acid at the position corresponding to G78 is substituted by an amino acid selected from the group consisting of Ala, Glu; Pro, Ser, and Tyr;
the amino acid at the position corresponding to Y131 is substituted by an amino acid selected from the group consisting of Ala, Asn, Asp, Cys, Gln; Glu, Gly, His, Ile, Leu, Met, Ser, Thr, Trp, and Val;
the amino acid at the position corresponding to S172 is substituted by an amino acid selected from the group consisting of Ala, Cys, and Thr; and/or
the amino acid at the position corresponding to W193 is substituted by an amino acid selected from the group consisting of Phe, Ser, Thr, and Tyr.

In a further embodiment of the first aspect,
the amino acid at the position corresponding to F24 is substituted by Arg;
the amino acid at the position corresponding to S44 is substituted by Pro;
the amino acid at the position corresponding to D56 is substituted by His;
the amino acid at the position corresponding to G78 is substituted by Pro;
the amino acid at the position corresponding to Y131 is substituted by Met;
the amino acid at the position corresponding to S172 is substituted by Ala; and/or
the amino acid at the position corresponding to W193 is substituted by Ser.

In one embodiment of the first aspect, said amino acid sequence additionally differs from SEQ ID NO: 1 at least by one or more amino acid substitutions at one or more positions corresponding to R99, R107, K125, and K170 of native porcine trypsin according to SEQ ID NO: 1.

In one embodiment of the first aspect,
the amino acid at the position corresponding to R107 is not substituted by Pro; and/or
the amino acid at the position corresponding to K170 is not substituted by Ile or Phe.

In a further embodiment of the first aspect,
the amino acid at the position corresponding to R99 is substituted by an amino acid selected from the group consisting of Ala, Asn, Asp, Glu, Gly, His, Leu, Phe, Thr, Trp, and Tyr;
the amino acid at the position corresponding to R107 is substituted by an amino acid selected from the group consisting of Asp, Gly, Pro, Ser, and Thr;
the amino acid at the position corresponding to K125 is substituted by an amino acid selected from the group consisting of Ala, Cys, Gln, Glu, Gly, His, Leu, Ser, and Tyr; and/or
the amino acid at the position corresponding to K170 is substituted by an amino acid selected from the group consisting of Ala, Asn, Gly, and Tyr.

In a further embodiment of the first aspect,
the amino acid at the position corresponding to R99 is substituted by an amino acid selected from the group consisting of Ala, His, and Asn;
the amino acid at the position corresponding to R107 is substituted by Thr;
the amino acid at the position corresponding to K125 is substituted by an amino acid selected from the group consisting of Ala, Cys, and Ser; and/or
the amino acid at the position corresponding to K170 is substituted by Ala.

In one embodiment of the first aspect, said amino acid sequence has at least 91% or at least 92% or at least 93% or at least 94% or at least 95% or at least 96% or at least 97% or at least 98% or at least 99% sequence identity with porcine wild-type trypsin according to SEQ ID NO: 1.

In one embodiment of the first aspect, said amino acid sequence differs from porcine wild-type trypsin according to SEQ ID NO: 1 by 1, 2, 3, 4, 5, 6, 7, 8, 9, 10, 11, 12, 13, 14, 15, 16, 17, 18, 19, 20, 21, 22, or 23 amino acid exchanges.

In one embodiment of the first aspect, said amino acid sequence is SEQ ID NO: 3, wherein
Xaa24 is an amino acid selected from the group consisting of Ala, Asn, Arg, Gln, Ile, Leu, Lys, Met, Phe, Ser, Thr, and Val;
Xaa44 is an amino acid selected from the group consisting of Leu, Pro, and Ser;
Xaa56 is an amino acid selected from the group consisting of Ala, Asn, Asp, His, and Trp;
Xaa78 is an amino acid selected from the group consisting of Ala, Glu, Gly, Pro, Ser, and Tyr;

Xaa99 is an amino acid selected from the group consisting of Ala, Arg, Asn, Asp, Glu, Gly, His, Leu, Phe, Thr, Trp, and Tyr;
Xaa107 is an amino acid selected from the group consisting of Arg, Asp, Gly, Pro, Ser, and Thr;
Xaa125 is an amino acid selected from the group consisting of Ala, Cys, Gln, Glu, Gly, His, Leu, Lys, Ser, and Tyr;
Xaa131 is an amino acid selected from the group consisting of Ala, Asn, Asp, Cys, Gln; Glu, Gly, His, Ile, Leu, Met, Ser, Thr, Trp, Tyr, and Val;
Xaa170 is an amino acid selected from the group consisting of Ala, Asn, Gly, Lys, and Tyr;
Xaa172 is an amino acid selected from the group consisting of Ala, Cys, Ser, and Thr; and/or
Xaa193 is an amino acid selected from the group consisting of Phe, Ser, Thr, Trp, and Tyr; with the proviso that SEQ ID NO: 3 is not porcine wild-type trypsin according to SEQ ID NO: 1; and with the proviso that SEQ ID NO: 3 is not porcine variant trypsin S172A according to SEQ ID NO: 2.

In a further embodiment of the first aspect, said amino acid sequence is SEQ ID NO: 3, wherein
Xaa24 is an amino acid selected from the group consisting of Phe and Arg;
Xaa44 is an amino acid selected from the group consisting of Ser and Pro;
Xaa56 is an amino acid selected from the group consisting of Asp and His;
Xaa78 is an amino acid selected from the group consisting of Gly and Pro;
Xaa99 is an amino acid selected from the group consisting of Ala, Arg, His and Asn;
Xaa107 is an amino acid selected from the group consisting of Arg and Thr;
Xaa125 is an amino acid selected from the group consisting of Ala, Cys, Lys and Ser;
Xaa131 is an amino acid selected from the group consisting of Met and Tyr;
Xaa170 is an amino acid selected from the group consisting of Ala and Lys;
Xaa172 is an amino acid selected from the group consisting of Ala and Ser; and/or
Xaa193 is an amino acid selected from the group consisting of Ser and Trp;
with the proviso that SEQ ID NO: 3 is not porcine wild-type trypsin according to SEQ ID NO: 1; and
with the proviso that SEQ ID NO: 3 is not porcine variant trypsin S172A according to SEQ ID NO: 2.

In one embodiment of the first aspect, said amino acid sequence is selected from the group consisting of SEQ ID NOs: 4 to 119. In one embodiment, said amino acid sequence is selected from the group consisting of SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, and SEQ ID NO: 98.

In one embodiment of the first aspect, said variant is capable of cleaving a peptide with the general formula A-Lys-Thr-Arg-Arg-B (SEQ ID NO: 131) to yield a cleavage product of the general formula A-Lys-Thr-Arg-Arg (SEQ ID NO: 132) in a yield of at least 80% (e.g. at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%), wherein A is an amino acid sequence consisting of one or more amino acids; and wherein B is an amino acid sequence consisting of one or more amino acids.

In further embodiments of the first aspect, A is an amino acid sequence consisting of between 1 and 105 amino acids (e.g. 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or 105 amino acids) and B is an amino acid sequence consisting of between 1 and 105 amino acids (e.g. 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or 105 amino acids).

In one embodiment of the first aspect, the variant exhibits an increased selectivity for the cleavage of a pre-pro-human insulin, pre-pro-insulin glargine, pre-pro-insulin lispro, pre-pro-insulin aspart, or pre-pro-insulin glulisine at a position C-terminally to position B32-Arg as compared to porcine variant trypsin S172A according to SEQ ID NO: 2.

In some embodiments of the first aspect of the present invention, the variant of porcine trypsin is lyophilized.

In a second aspect, the present invention is directed to a nucleic acid molecule encoding
 a variant of porcine trypsin as defined in the first aspect of the invention; or
 a trypsinogen precursor molecule of a variant of porcine trypsin as defined in the first aspect of the invention.

In one embodiment of the second aspect, said nucleic acid molecule is contained in a vector or is integrated into a genome.

In a third aspect, the present invention is directed to a host cell containing a nucleic acid molecule as defined in the second aspect. In one embodiment, the host cell is a recombinant host cell.

In a fourth aspect, the present invention is directed to a method of producing a variant of porcine trypsin of the present invention comprising the steps of:
 cultivating a host cell according to the third aspect; and
 isolating the trypsinogen precursor molecule of the variant of porcine trypsin from the culture medium or from the host cell.

In one embodiment of the fourth aspect, the method contains the further step:
 activating the trypsinogen precursor molecule, thereby obtaining said variant of porcine trypsin.

Activation of the trypsinogen precursor molecule can be accomplished chemically or enzymatically. For example, the pH can be adjusted so that auto-activation occurs. In another example, a protease (e.g. enterokinase) can be added to activate the trypsinogen enzymatically.

In a fifth aspect, the present invention is directed to a variant of porcine trypsin of the present invention or a nucleic acid molecule of the present invention or a host cell of the present invention for use as a medicament; for use as a food ingredient; for use as a feed ingredient or for use within a process of manufacturing a food ingredient or a feed ingredient.

One embodiment of the fifth aspect is directed to a variant of porcine trypsin of the present invention for use as a food ingredient; for use as a feed ingredient or for use within a process of manufacturing a food ingredient or a feed ingredient.

In one embodiment of the fifth aspect, the medicament is for use in the treatment of swelling (especially swelling caused by trauma), inflammation (especially inflammation caused by trauma), thrombophlebitis, activated arthrosis, deficiency of digestive enzymes (e.g. caused by pancreas insufficiency), and/or digestive disorders.

In other words, the present invention is directed to a variant of porcine trypsin of the present invention or a nucleic acid molecule of the present invention or a host cell of the present invention for use in the treatment of swelling (especially swelling caused by trauma), inflammation (especially inflammation caused by trauma), thrombophlebitis, activated arthrosis, deficiency of digestive enzymes (e.g. caused by pancreas insufficiency), and/or digestive disorders.

With respect to the usage as food ingredient, as feed ingredient or within a manufacturing process, the fifth aspect can alternatively be worded as follows:

Use of a variant of porcine trypsin of the present invention as a food ingredient.

Use of a variant of porcine trypsin of the present invention as a feed ingredient.

Use of a variant of porcine trypsin of the present invention in a process of manufacturing a food ingredient or a feed ingredient.

In a sixth aspect, the present invention is directed to a use of the variant of porcine trypsin of the present invention in a method for the production of human insulin, an insulin analogue or a derivative of insulin.

The sixth aspect encompasses the use of variants of porcine trypsin of the invention both in in vitro methods and in in vivo methods for the production of human insulin, an insulin analogue or a derivative of insulin.

With respect to the usage in in vivo methods, the sixth aspect can alternatively be worded as follows:

A variant of porcine trypsin according to the first aspect for use in the in vivo production of human insulin, an insulin analogue or a derivative of insulin.

In one embodiment of the sixth aspect, the insulin analogue is selected from the group consisting of insulin aspart, insulin lispro, insulin glulisine, and insulin glargine.

In a seventh aspect, the present invention is directed to a use of a variant of porcine trypsin of the present invention to cleave a protein or peptide with the general formula A-Lys-Thr-Arg-Arg-B (SEQ ID NO: 131), wherein A is an amino acid sequence consisting of one or more amino acids; and wherein B is an amino acid sequence consisting of one or more amino acids.

In further embodiments of the seventh aspect, A is an amino acid sequence consisting of between 1 and 105 amino acids (e.g. 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or 105 amino acids) and B is an amino acid sequence consisting of between 1 and 105 amino acids (e.g. 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100, or 105 amino acids).

In one embodiment of the seventh aspect, the cleavage yields a cleavage product A-Lys-Thr-Arg-Arg (SEQ ID NO: 132). In further embodiments of the seventh aspect, the cleavage yields the cleavage product A-Lys-Thr-Arg-Arg (SEQ ID NO: 132) in a yield of at least 80% (e.g. at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%).

In an eighth aspect, the present invention is directed to a composition comprising a variant of porcine trypsin of the present invention or a nucleic acid molecule of the present invention or a host cell of the present invention.

In one embodiment of the eighth aspect, the composition further comprises an excipient and/or at least one other active agent.

In some embodiments of the eighth aspect, the composition is a pharmaceutical composition.

In some embodiments of the eighth aspect the composition or the pharmaceutical composition is lyophilized.

The present invention also provides a combination of a variant of porcine trypsin of the present invention (or a nucleic acid molecule of the present invention or a host cell of the present invention) with at least one other active pharmaceutical ingredient. In one embodiment, the combination of the variant of porcine trypsin of the present invention with at least one other active pharmaceutical ingredient can be applied either by separate administration of the active pharmaceutical ingredient to the patient or in the form of combination products in which a plurality of active pharmaceutical ingredients are present in one pharmaceutical composition. When administered separately, administration may occur simultaneously or sequentially, in any order. The amount of the active agent of the invention and the other active pharmaceutical ingredient(s) and the relative timings of administration will be selected in order to achieve the desired combined therapeutic effect. The administration of the combination may be concomitantly in: (1) a unitary pharmaceutical composition including all active pharmaceutical ingredients; or (2) separate pharmaceutical compositions each including at least one of the active pharmaceutical ingredients. Alternatively, the combination may be administered separately in a sequential manner wherein one treatment agent is administered first and the other second or vice versa. Such sequential administration may be close in time or remote in time.

EXAMPLES

The following examples are put forth so as to provide those of ordinary skill in the art with a complete disclosure and description of how to make and use the compounds, compositions, and methods of the invention, and are not intended to limit the scope of the invention as indicated by the appended claims in any way. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Mutagenesis of the Synthetic Nucleotide Sequence that Encodes Porcine Trypsin and Cloning The improvement of enzymes can be achieved by enzyme engineering. This technique involves the development of variants of a starting enzyme with improved properties. For providing the enzyme variants, first the mutations were introduced at the gene level in the synthetic nucleotide sequence that encodes porcine pancreatic trypsin by usual molecular-biological methods. The genes of the enzyme variants were cloned into the expression vector pLE1A17 (derivative of pRSF-1 b, Novagen). The resulting plasmids were used for transformation of E. coli BL21 (DE3) cells.

Example 2: Expression of Variant Porcine Trypsinogen

The recombinant expression of porcine trypsinogen in E. coli was performed by autoinduction according to F. W. Studier (F. W. Studier (2005) Prot. Exp. Pur. 41:207-234)

using medium ZYM-5052 supplemented with kanamycin (50 mg/L) at 30° C. Once the glucose in the culture is metabolised the present lactose induces the expression. Glycerol was used as C-source. The expression was conducted on microplate as well as on shake flask scale.

For shake flask experiments, a pre culture of 20 mL medium ZYM-505 supplemented with kanamycin (50 mg/L) with 50 µL glycerol (36%) was incubated for 24 h at 30° C. and 200 rpm. An OD600 of 12.5-14 was achieved. For the main culture 500 µL of pre culture were used to inoculate 100 mL medium ZYM-5052, supplemented with kanamycin (50 mg/L). After incubation for 24 h at 30° C. and 200 rpm an OD600 of 6.5-7.5 was achieved. After centrifugation, cell pellets were stored at −20° C.

Example 3: Cell Disruption and Trypsinogen Activation

The periplasmatic trypsinogen was liberated by osmotic shock. 3.6 g cells (obtained from Example 2) were resuspended in 10 mL of lysis buffer (10 mM Tris-HCl, pH=8, 25 mM $MgCl_2$, 200 mM NaCl) until a homogenous suspension is obtained. The suspension was stirred for 24 h at 5° C. and 180 rpm. After centrifugation the supernatant was subjected to activation. For activation of the trypsinogen, enterokinase from porcine intestine was used (Sigma, product no. E0885; 40 units; Unit definition: One unit enterokinase will produce 1.0 nanomole of trypsin from trypsinogen per minute at pH 5.6 at 25° C.).

Enterokinase was added to the cell free extract to a final concentration of 17 mU/mL. The reaction was incubated for 16-24 h at 30° C. The resulting trypsin solution was stored at −20° C.

Example 4: Assay to Determine the Tryptic Activity of Purified Variant Recombinant Porcine Trypsin The activity of trypsin was determined using Chromozym TRY (Roche Diagnostics GmbH) in 100 mM Tris pH 8.0, 20 mM $CaCl_2$ at 25° C. Chromozym TRY is substrate (Carbobenzoxy-L-valyl-L-glycyl-L-arginine-4-nitranilide acetate) for the reliable photometrical determination of activity of proteases which hydrolyze peptides at the carboxylic side of arginine (trypsin, endoproteinase Arg-C and others). Photometric measurement was carried out at 405 nm.

Example 5: Screening Results with Pre-Pro Human Insulin

Initial screening of all trypsin variants was performed with pre-pro-human insulin (PPI) as a model system. The PPI was solved in buffered solution (pH=8.3) up to a concentration of 0.75 g/L. Trypsin variant solution was prepared according to example 3 and added to the reaction mixture without further processing. Samples were taken periodically, acidified with 1 N HCl and analyzed by HPLC (Example 7).

Two aspects were considered: (1) whether the trypsin variant shows any PPI cleavage activity (results shown in Table 1, Column A); (2) whether the trypsin variant shows PPI cleavage activity: if the trypsin cleavage selectivity is improved in comparison to SEQ ID NO: 2 (results shown in Table 1, Column B) In order to evaluate the di-Arg selectivity of the trypsin variants, the formation of B31Arg-B32Arg-human insulin has been monitored by HPLC (see Example 7) and compared to SEQ ID NO: 2. The selectivity has been calculated according to $$\text{Selectivity} = \frac{[diArg]}{[diArg] + [monoArg] + [desThr] + [UI]} \cdot 100\%$$

with
[diArg]=concentration of B31Arg-B32Arg-human insulin
[monoArg]=concentration of desB32Arg-insulin human
[desThr]=concentration of desB30Thr-insulin human
[UI]=concentration of an unknown cleavage intermediate

TABLE 1

| Screening results with pre-pro human insulin | | |
|---|---|---|
| Mutant SEQ ID NO: | A Activity PPI cleavage | B Selectivity |
| 2 | yes | 62.1% |
| 4 | yes | >90% |
| 5 | yes | >90% |
| 6 | yes | >90% |
| 7 | yes | >90% |
| 8 | yes | >90% |
| 9 | yes | >90% |
| 10 | yes | >90% |
| 11 | yes | >90% |
| 12 | yes | >90% |
| 13 | yes | >90% |
| 14 | yes | >90% |
| 15 | yes | >90% |
| 16 | yes | >90% |
| 17 | yes | >80% |
| 18 | yes | >90% |
| 19 | yes | >90% |
| 20 | yes | >90% |
| 21 | yes | >90% |
| 22 | yes | >90% |
| 23 | yes | >90% |
| 24 | yes | >90% |
| 25 | yes | >90% |
| 26 | yes | >80% |
| 27 | yes | >80% |
| 28 | yes | >90% |
| 29 | yes | >90% |
| 30 | yes | >70% |
| 31 | yes | >62.1% |
| 32 | yes | >90% |
| 33 | yes | >90% |
| 34 | yes | >90% |
| 35 | yes | >90% |
| 36 | yes | >90% |
| 37 | yes | >90% |
| 38 | yes | >80% |
| 39 | yes | >90% |
| 40 | yes | >80% |
| 41 | yes | >90% |
| 42 | yes | >90% |
| 43 | yes | >80% |
| 44 | yes | >80% |
| 45 | yes | >65% |
| 46 | yes | >70% |
| 47 | yes | >90% |
| 48 | yes | >80% |
| 49 | yes | >80% |
| 50 | yes | >65% |
| 51 | yes | >70% |
| 52 | yes | >90% |
| 53 | yes | >90% |
| 54 | yes | >90% |
| 55 | yes | >90% |
| 56 | yes | >90% |
| 57 | yes | >90% |
| 58 | yes | >90% |
| 59 | yes | >90% |
| 60 | yes | >90% |

TABLE 1-continued

Screening results with pre-pro human insulin

| Mutant SEQ ID NO: | A Activity PPI cleavage | B Selectivity |
|---|---|---|
| 61 | yes | >80% |
| 62 | yes | >90% |
| 63 | yes | >90% |
| 64 | yes | >90% |
| 65 | yes | >80% |
| 66 | yes | >90% |
| 67 | yes | >90% |
| 68 | yes | >70% |
| 69 | yes | >70% |
| 70 | yes | >70% |
| 71 | yes | >62.1% |
| 72 | yes | >90% |
| 73 | yes | >90% |
| 74 | yes | >90% |
| 75 | yes | >90% |
| 76 | yes | >90% |
| 77 | yes | >90% |
| 78 | yes | >80% |
| 79 | yes | >90% |
| 80 | yes | >90% |
| 81 | yes | >90% |
| 82 | yes | >90% |
| 83 | yes | >90% |
| 84 | yes | >90% |
| 85 | yes | >90% |
| 86 | yes | >90% |
| 87 | yes | >90% |
| 88 | yes | >90% |
| 89 | yes | >90% |
| 90 | yes | >90% |
| 91 | yes | >90% |
| 92 | yes | >90% |
| 93 | yes | >90% |
| 94 | yes | >90% |
| 95 | yes | >90% |
| 96 | yes | >90% |
| 97 | yes | >90% |
| 98 | yes | >90% |
| 99 | yes | >80% |
| 100 | yes | >90% |
| 101 | yes | >90% |
| 102 | yes | >90% |
| 103 | yes | >90% |
| 104 | yes | >90% |
| 105 | yes | >90% |
| 106 | yes | >90% |
| 107 | yes | >90% |
| 108 | yes | >80% |
| 109 | yes | >90% |
| 110 | yes | >90% |
| 111 | yes | >80% |
| 112 | yes | >90% |
| 113 | yes | >90% |
| 114 | yes | >90% |
| 115 | yes | >90% |
| 116 | yes | >90% |
| 117 | yes | >90% |
| 118 | yes | >90% |
| 119 | yes | >90% |
| 120 | yes | 1.4% |
| 121 | yes | 4.6% |
| 122 | yes | 59.4% |
| 123 | yes | 60.7% |
| 124 | yes | 27.6% |
| 125 | yes | 12.2% |
| 126 | yes | 7.2% |
| 127 | yes | 20.5% |
| 128 | yes | 57.1% |
| 129 | yes | 44.8% |
| 130 | yes | 33.8% |

Example 6: Cleavage of Pre-Pro-Insulin Glargine Using Recombinant SEQ ID NO: 2 (Trypsin Variant S172A) and the Optimized Variants Thereof These experiments were conducted at 20° C. and a pH value of 8.3 (buffered solution) and were performed up to the 1000 mL scale.

The pre-pro-insulin glargine solution was filled in an appropriate thermostated reaction vessel and the reaction was started by addition of the solution of a variant of porcine trypsin. Samples were taken after definite time intervals; the enzymatic reaction was immediately stopped by acidifying the sample solution using 1 N or 2 N HCl solution. The samples were analysed by HPLC (see Example 7).

Figure 2:
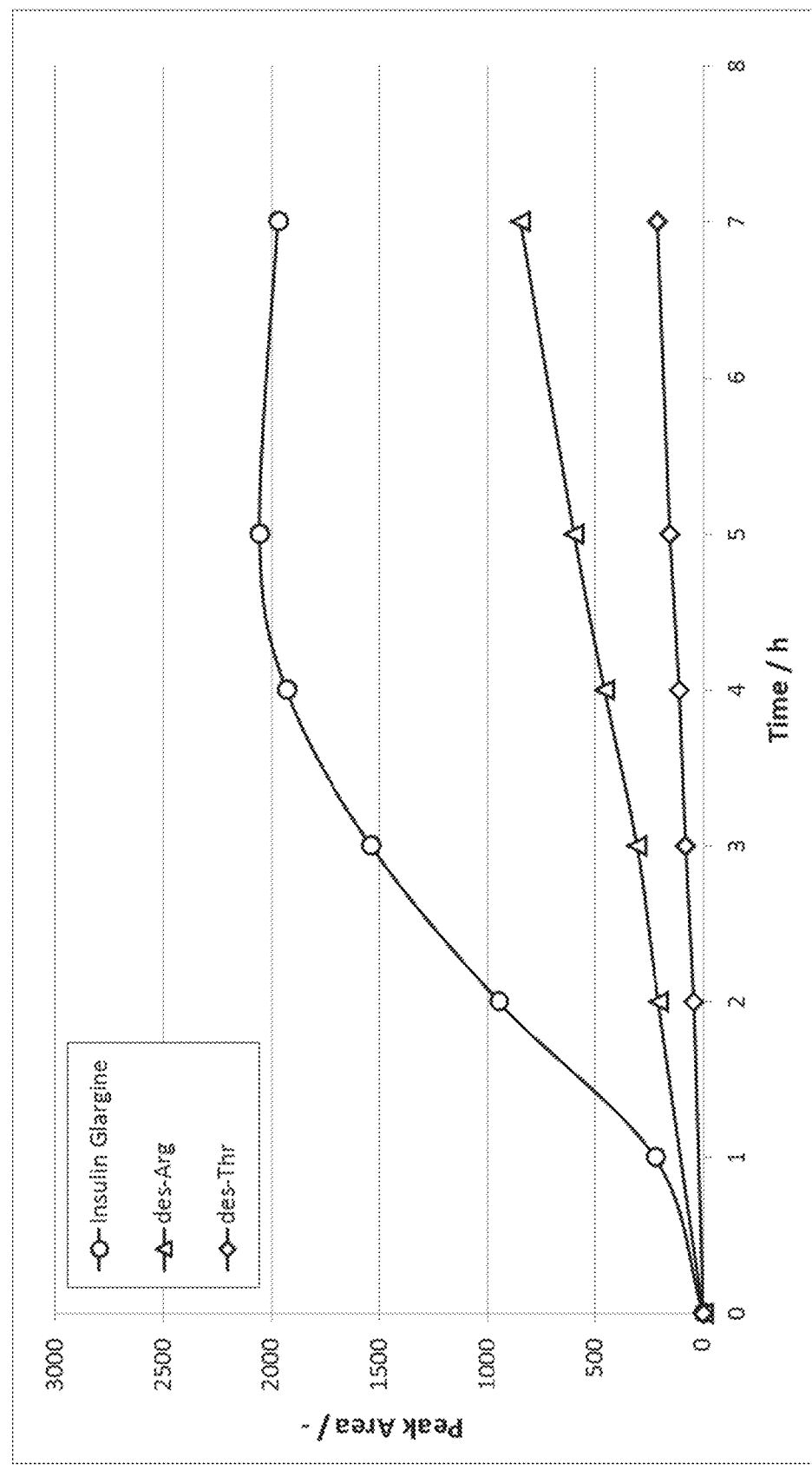
FIG. 2 shows the cleavage of pre-pro-insulin glargine with trypsin variant S172A (SEQ ID NO: 2). The Figure shows the time-dependent course of the formation of insulin glargine as well as the formation of the most prominent cleavage by-products B31Arg-insulin glargine (cleavage after position 31 in insulin glargine B-chain, abbreviated as "des-Arg" in the FIG. and desB30Thr insulin glargine (cleavage after position 29 of insulin glargine B-chain, abbreviated as "des-Thr" in the Figure).

FIG. 2 shows the reaction kinetics of SEQ ID NO: 2. The Figure shows the time-dependent course of the formation of insulin glargine as well as the formation of the most prominent cleavage by-products B31Arg-insulin glargine) (cleavage after position 31 in insulin glargine B-chain, referred to as "des-Arg") and desB30Thr insulin glargine (cleavage after position 29 of insulin glargine B-chain, referred to as "des-Thr").

Figure 4:
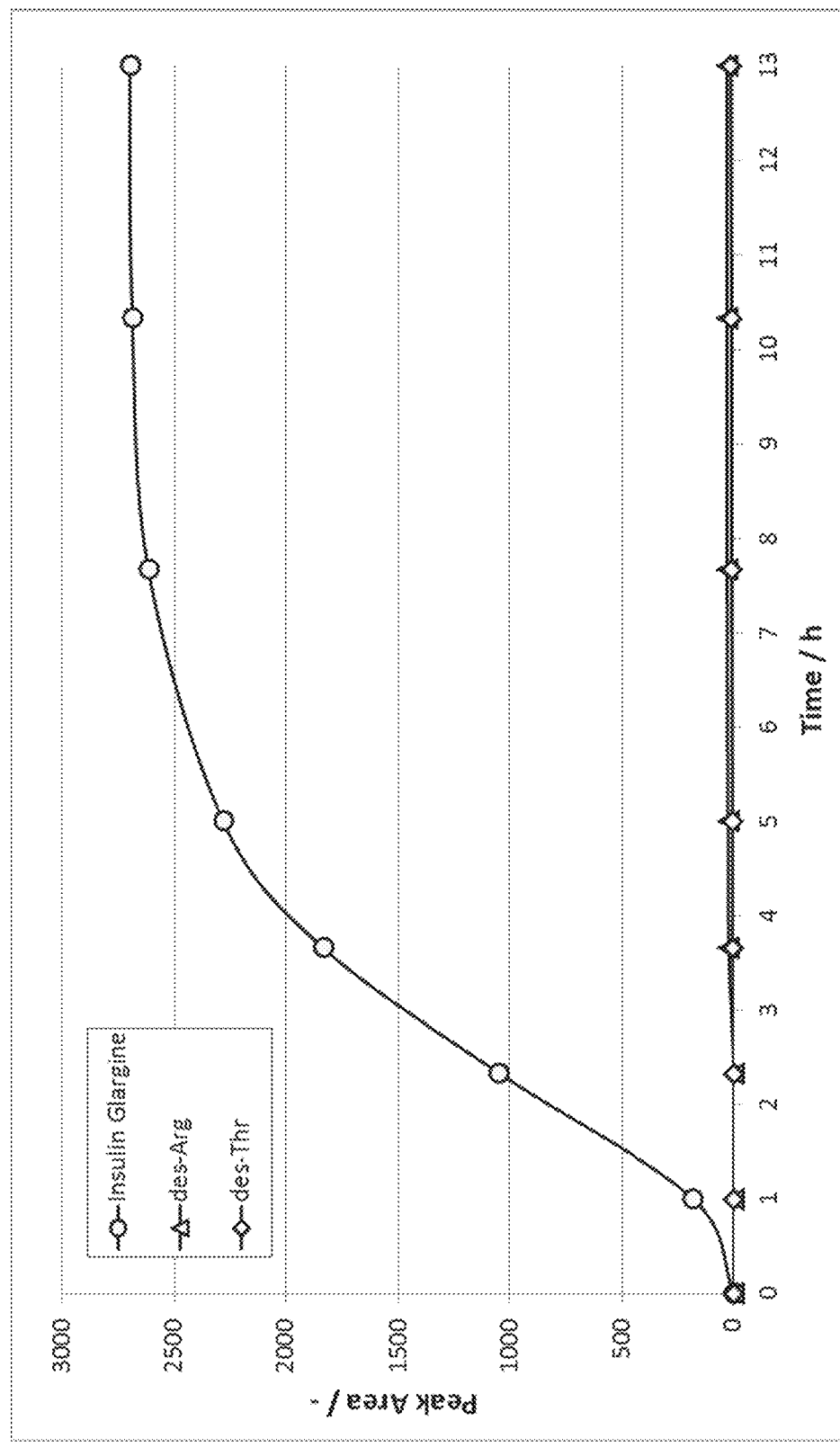
FIG. 4 shows the cleavage of pre-pro-insulin glargine with the trypsin variant no. 105 (SEQ ID NO: 105) as an example for a cleavage with an optimized trypsin variant. The Figure shows the time-dependent course of the formation of insulin glargine as well as the reduced formation of the most prominent cleavage by-products B31Arg-insulin glargine (cleavage after position 31 in insulin glargine B-chain, abbreviated as "des-Arg" in the Figure) and desB30Thr insulin glargine (cleavage after position 29 of insulin glargine B-chain, abbreviated as "des-Thr" in the Figure).

Selected variants have been subjected to a cleavage of pre-pro-insulin Glargine. The results are depicted in Table 2. The content of insulin glargine, desB32Arg-insulin glargine and desB29Thr-insulin glargine is given in form of peak area from an analytical HPLC chromatogram at the end of the cleavage and represents the ratio of insulin glargine and the side products. Furthermore the molar cleavage yield is given according to $$\text{Yield} = \frac{n(\text{insulin Glargine})}{n(pre-pro-\text{insulin Glargine})} \cdot 100\%$$

with
n(insulin Glargine)=moles of insulin Glargine formed
n(pre-pro-insulin Glargine)=moles of pre-pro-insulin Glargine deployed FIG. 4 shows the reaction kinetics of porcine trypsin variant no. 105 (SEQ ID NO: 105) as an example for an optimized trypsin variant.

TABLE 2

Comparison of cleavage results with pre-pro-insulin glargine

| Mutant SEQ ID NO: | Purity | | | Yield % |
|---|---|---|---|---|
| | Insulin Glargine area % | desArg area % | desThr area % | |
| 2 | 53.6 | 19.1 | 5.2 | 65 |
| 4 | 86.4 | <0.5 | 2.9 | >90 |
| 9 | 85.2 | <0.5 | 3.6 | >90 |
| 10 | 82.7 | <0.5 | 2.6 | >90 |
| 11 | 84.1 | <0.5 | 2.2 | >90 |
| 14 | 84.5 | <0.5 | 2.4 | >90 |
| 18 | 82.6 | <0.5 | 1.9 | >80 |
| 19 | 81.0 | <0.5 | 3.3 | >80 |
| 24 | 82.3 | <0.5 | 2.8 | >80 |
| 25 | 80.4 | <0.5 | 2.8 | >80 |
| 36 | 87.6 | <0.5 | 1.5 | >90 |
| 41 | 82.8 | <0.5 | 1.9 | >90 |
| 53 | 81.3 | <0.5 | 2.1 | >80 |
| 56 | 85.3 | <0.5 | 2.0 | >90 |
| 57 | 87.5 | <0.5 | 2.3 | >90 |
| 73 | 83.0 | <0.5 | 2.2 | >90 |
| 74 | 82.4 | <0.5 | 2.1 | >80 |
| 77 | 88.2 | 0.5 | 1.6 | >90 |

TABLE 2-continued

Comparison of cleavage results with pre-pro-insulin glargine

| Mutant SEQ ID NO: | Insulin Glargine area % | desArg area % | desThr area % | Yield % |
|---|---|---|---|---|
| 78 | 85.1 | 0.5 | 1.6 | >90 |
| 79 | 87.8 | 0.7 | 0.3 | >90 |
| 80 | 90.1 | 0.9 | 0.5 | >90 |
| 81 | 89.7 | 1.2 | 0.5 | >90 |
| 82 | 83.8 | 0.6 | 0.3 | >80 |
| 83 | 89.0 | <0.5 | 1.2 | >90 |
| 84 | 85.4 | 0.6 | 1.6 | >90 |
| 85 | 85.4 | 1.1 | 0.2 | >90 |
| 86 | 79.3 | 0.8 | 0.1 | >80 |
| 87 | 83.8 | 0.6 | 0.3 | >80 |
| 88 | 84.3 | 0.7 | 1.9 | >90 |
| 89 | 88.1 | 0.5 | 1.2 | >90 |
| 90 | 89.5 | 0.9 | 0.2 | >90 |
| 91 | 86.8 | 1.0 | 0.3 | >90 |
| 92 | 88.1 | 0.9 | 0.6 | >90 |
| 93 | 71.3 | 0.7 | 0.3 | >75 |
| 94 | 85.2 | 0.8 | 0.3 | >90 |
| 95 | 90.0 | 1.0 | 0.6 | >90 |
| 96 | 78.7 | 0.7 | 0.3 | >80 |
| 97 | 89.4 | <0.5 | 1.2 | >90 |
| 98 | 89.4 | 0.9 | 2.7 | >90 |
| 99 | 89.2 | 0.9 | 1.0 | >90 |
| 100 | 80.0 | 0.7 | 0.3 | >80 |
| 101 | 89.2 | 1.0 | 0.4 | >90 |
| 102 | 88.7 | 0.4 | 1.2 | >90 |
| 103 | 90.7 | 0.9 | 1.4 | >90 |
| 104 | 89.3 | 1.1 | 1.0 | >90 |
| 105 | 88.9 | 1.0 | 0.9 | >90 |
| 106 | 86.8 | 0.7 | 1.0 | >90 |
| 107 | 88.1 | 0.4 | 1.3 | >90 |
| 108 | 88.8 | 0.8 | 0.7 | >90 |
| 109 | 85.9 | 0.7 | 0.5 | >80 |
| 110 | 90.6 | 0.9 | 0.6 | >90 |
| 111 | 85.9 | 0.7 | 2.6 | >90 |
| 113 | 86.1 | 0.5 | 1.7 | >90 |
| 115 | 83.5 | 0.8 | 0.6 | >90 |
| 116 | 82.7 | 0.5 | 0.6 | >90 |
| 117 | 85.0 | 0.6 | 0.8 | >90 |
| 118 | 87.6 | 0.6 | 1.0 | >90 |
| 119 | 85.2 | 0.6 | 1.0 | >90 |

As can be clearly seen from Table 2, the optimized trypsin variants show an enhanced cleavage selectivity towards pre-pro-insulin glargine resulting in a significantly increased yield accompanied with a reduced impurity profile, considering B31Arg-insulin glargine (desArg) and desB30Thr-insulin glargine (desThr). Comparison of Table 1 and 2 shows a very high comparability of the cleavage results obtained with pre-pro-insulin human and pre-pro-insulin Glargine.

Example 7: HPLC Method

| | |
|---|---|
| Method | High performance liquid chromatography |
| Column | Manufacturer: Macherey & Nagel |
| | Brand: Nucleosil 120-5 C18 |
| | Dimension: 250 × 4 mm |
| Mobile Phase A: | 45 mM sodium phosphate buffer (pH 2.5). 315 mM NaCl. 25% (v/v) acetonitrile |
| Mobile Phase B | 45 mM sodium phosphate buffer (pH 2.5). 55 mM NaCl. 65% (v/v) acetonitrile |

| | time/min | Mobile Phase A | Mobile Phase B |
|---|---|---|---|
| Gradient | 0 min | 94% | 6% |
| | 30 min linear | 90% | 10% |
| Injection volume: | | 5 µL | |
| Detection: | | UV (215 nm) | |

Example 8: Exopeptidase Activity

These experiments were conducted at 8° C. and a pH value of 8.3 (buffered solution). The insulin glargine solution (0.5 g/L) was filled into an appropriate thermostated reaction vessel and the reaction was started by addition of SEQ ID NO: 2 solution (100 U/g$_{insulin}$) Samples were taken after definite time intervals and the enzymatic reaction was immediately stopped by acidifying the sample solution using 1 N HCl solution. The samples were analysed by HPLC (see Example 7). The reaction kinetics are depicted in FIG. 3.

Figure 3:
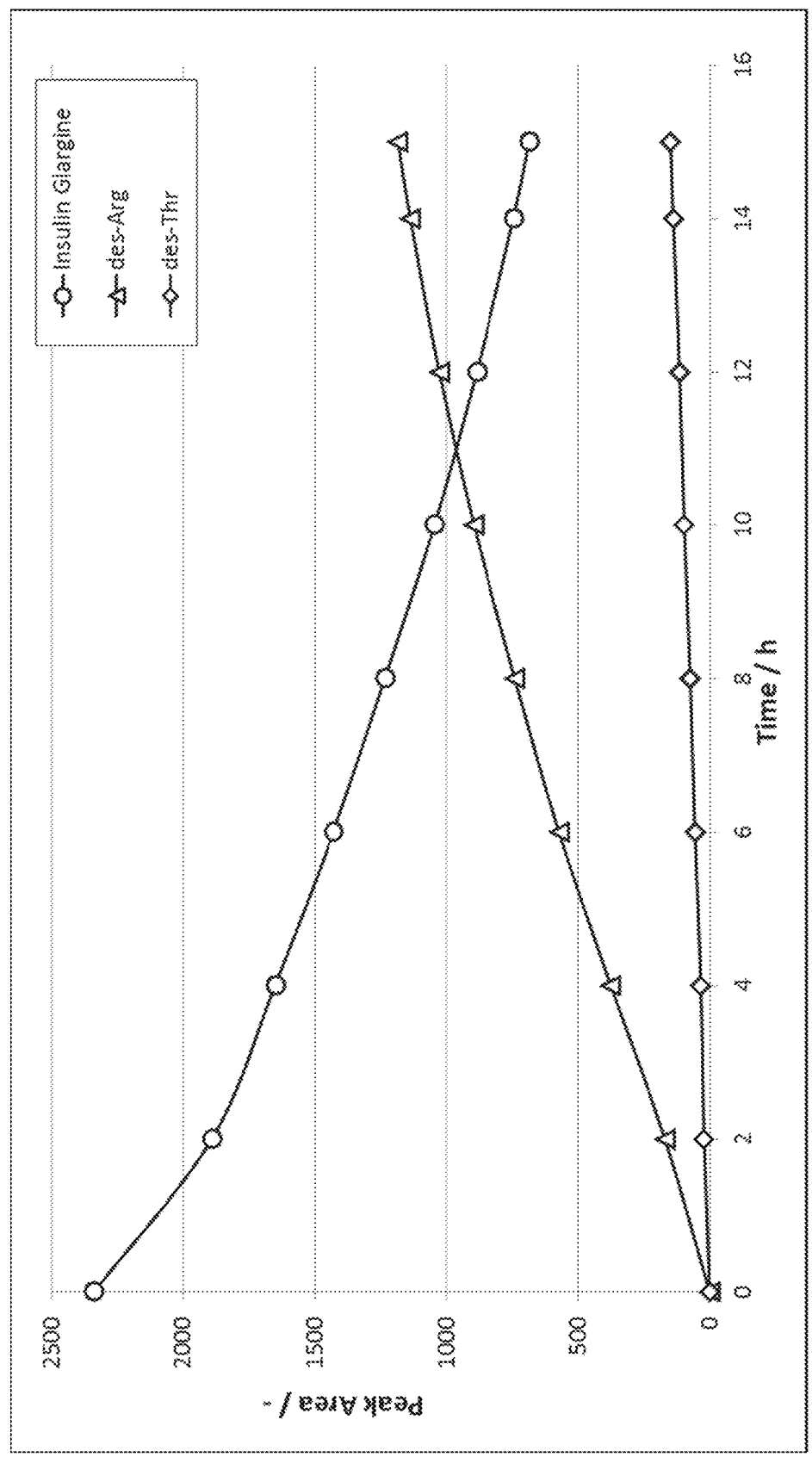
FIG. 3 shows the cleavage of insulin glargine with trypsin variant S172A (SEQ ID NO: 2) as an example for the exopeptidase activity of trypsin variant S172A. The Figure shows the time-dependent decrease of insulin glargine as well as the formation of the main product B32-desArg-insulin glargine (cleavage after position 31 in insulin glargine B-chain, abbreviated as "des-Arg" in the Figure) and small amounts of the by-product B30-desThr insulin glargine (cleavage after position 29 of insulin glargine B-chain, abbreviated as "des-Thr" in the Figure).

As can be clearly seen in FIG. 3, the concentration of insulin glargine is decreased over time. Beside the formation of a small amount of B30-desThr-insulin glargine, the main product formed in this reaction is B32-desArg-insulin glargine indicating that trypsin SEQ ID NO: 2 is able to cleave off a single arginine at position B32 by means of an exopeptidase activity.

TABLE 3

List of Trypsin Variants

| SEQ ID NO: | F24 | S44 | D56 | G78 | R99 | R107 | K125 | Y131 | K170 | S172 | W193 |
|---|---|---|---|---|---|---|---|---|---|---|---|
| 1 | F | S | D | G | R | R | K | Y | K | S | W |
| 2 | F | S | D | G | R | R | K | Y | K | A | W |
| 3 | X | X | X | X | X | X | X | X | X | X | X |
| 4 | R | S | D | G | A | R | K | Y | K | A | S |
| 5 | R | S | D | G | L | R | K | Y | K | A | S |
| 6 | R | S | D | G | F | R | K | Y | K | A | S |
| 7 | R | S | D | G | W | R | K | Y | K | A | S |
| 8 | R | S | D | G | G | R | K | Y | K | A | S |
| 9 | R | S | D | G | Y | R | K | Y | K | A | S |
| 10 | R | S | D | G | T | R | K | Y | K | A | S |
| 11 | R | S | D | G | N | R | K | Y | K | A | S |
| 12 | R | S | D | G | D | R | K | Y | K | A | S |
| 13 | R | S | D | G | E | R | K | Y | K | A | S |
| 14 | R | S | D | G | H | R | K | Y | K | A | S |
| 15 | R | S | D | G | R | A | K | Y | K | A | S |
| 16 | R | S | D | G | R | G | K | Y | K | A | S |
| 17 | R | S | D | G | R | R | Y | Y | K | A | S |

TABLE 3-continued

List of Trypsin Variants

| SEQ ID NO: | F24 | S44 | D56 | G78 | R99 | R107 | K125 | Y131 | K170 | S172 | W193 |
|---|---|---|---|---|---|---|---|---|---|---|---|
| 18 | R | S | D | G | R | R | S | Y | K | A | S |
| 19 | R | S | D | G | R | R | C | Y | K | A | S |
| 20 | R | S | D | G | R | R | E | Y | K | A | S |
| 21 | R | S | D | G | R | R | H | Y | K | A | S |
| 22 | R | S | D | G | R | R | L | Y | K | A | S |
| 23 | R | S | D | G | R | R | Q | Y | K | A | S |
| 24 | R | S | D | G | R | R | K | Y | Y | A | S |
| 25 | R | S | D | G | R | R | K | Y | A | A | S |
| 26 | R | S | D | G | R | R | K | Y | G | A | S |
| 27 | R | S | D | G | R | R | K | Y | N | A | S |
| 28 | V | S | D | G | R | R | K | Y | K | A | S |
| 29 | L | S | D | G | R | R | K | Y | K | A | S |
| 30 | S | S | D | G | R | R | K | Y | K | A | S |
| 31 | Q | S | D | G | R | R | K | Y | K | A | S |
| 32 | R | S | D | G | R | R | K | Y | K | A | S |
| 33 | R | S | D | G | R | T | K | Y | K | A | S |
| 34 | R | S | D | G | R | R | K | A | K | A | S |
| 35 | R | S | D | G | R | R | K | L | K | A | S |
| 36 | R | S | D | G | R | R | K | M | K | A | S |
| 37 | R | S | D | G | R | R | K | T | K | A | S |
| 38 | R | S | D | G | R | R | K | C | K | A | S |
| 39 | R | S | D | G | R | R | K | N | K | A | S |
| 40 | R | S | D | G | R | R | K | E | K | A | S |
| 41 | R | S | D | G | R | R | K | H | K | A | S |
| 42 | R | S | D | G | R | R | K | Y | K | A | S |
| 43 | R | S | D | G | R | R | K | Y | K | T | S |
| 44 | R | S | D | G | R | R | K | Y | K | S | S |
| 45 | R | S | D | G | R | R | K | Y | K | C | S |
| 46 | A | S | D | G | R | R | K | Y | K | A | S |
| 47 | I | S | D | G | R | R | K | Y | K | A | S |
| 48 | M | S | D | G | R | R | K | Y | K | A | S |
| 49 | T | S | D | G | R | R | K | Y | K | A | S |
| 50 | N | S | D | G | R | R | K | Y | K | A | S |
| 51 | K | S | D | G | R | R | K | Y | K | A | S |
| 52 | R | L | D | G | R | R | K | Y | K | A | S |
| 53 | R | P | D | G | R | R | K | Y | K | A | S |
| 54 | R | S | A | G | R | R | K | Y | K | A | S |
| 55 | R | S | W | G | R | R | K | Y | K | A | S |
| 56 | R | S | N | G | R | R | K | Y | K | A | S |
| 57 | R | S | H | G | R | R | K | Y | K | A | S |
| 58 | R | S | D | G | R | P | K | Y | K | A | S |
| 59 | R | S | D | G | R | G | K | Y | K | A | S |
| 60 | R | S | D | G | R | S | K | Y | K | A | S |
| 61 | R | S | D | G | R | D | K | Y | K | A | S |
| 62 | R | S | D | G | R | R | K | V | K | A | S |
| 63 | R | S | D | G | R | R | K | I | K | A | S |
| 64 | R | S | D | G | R | R | K | W | K | A | S |
| 65 | R | S | D | G | R | R | K | G | K | A | S |
| 66 | R | S | D | G | R | R | K | S | K | A | S |
| 67 | R | S | D | G | R | R | K | Q | K | A | S |
| 68 | R | S | D | G | R | R | K | D | K | A | S |
| 69 | R | S | D | G | R | R | K | Y | K | A | F |
| 70 | R | S | D | G | R | R | K | Y | K | A | Y |
| 71 | R | S | D | G | R | R | K | Y | K | A | T |
| 72 | R | S | D | S | R | R | K | Y | K | A | S |
| 73 | R | S | D | A | R | R | K | Y | K | A | S |
| 74 | R | S | D | P | R | R | K | Y | K | A | S |
| 75 | R | S | D | Y | R | R | K | Y | K | A | S |
| 76 | R | S | D | E | R | R | K | Y | K | A | S |
| 77 | R | P | H | G | H | T | C | M | K | A | S |
| 78 | R | S | H | P | H | T | C | Y | K | A | S |
| 79 | R | P | H | P | H | R | A | M | K | A | S |
| 80 | R | S | H | P | H | T | S | M | K | A | S |
| 81 | R | S | H | P | H | T | A | M | K | A | S |
| 82 | R | P | H | P | H | R | C | M | K | A | S |
| 83 | R | P | H | P | N | T | S | M | K | A | S |
| 84 | R | P | H | P | N | T | S | M | K | S | S |
| 85 | R | P | H | P | H | T | C | M | K | A | S |
| 86 | R | P | D | P | A | T | S | M | K | A | S |
| 87 | R | P | H | P | H | T | S | M | K | A | S |
| 88 | R | P | H | P | H | T | S | M | K | S | S |
| 89 | R | P | H | P | H | T | A | M | K | A | S |
| 90 | R | P | H | P | H | T | A | M | K | S | S |
| 91 | R | P | H | P | A | T | S | M | K | A | S |
| 92 | R | P | H | P | A | T | C | M | K | A | S |

TABLE 3-continued

List of Trypsin Variants

| SEQ ID NO: | F24 | S44 | D56 | G78 | R99 | R107 | K125 | Y131 | K170 | S172 | W193 |
|---|---|---|---|---|---|---|---|---|---|---|---|
| 93 | R | S | D | P | N | T | C | M | A | A | S |
| 94 | R | P | H | G | N | R | C | M | A | A | S |
| 95 | R | P | H | P | H | R | S | M | A | A | S |
| 96 | R | P | D | P | H | R | S | M | A | A | S |
| 97 | R | P | H | P | A | T | A | M | A | A | S |
| 98 | R | P | H | P | A | T | A | M | A | S | S |
| 99 | R | S | H | P | N | T | S | Y | A | A | S |
| 100 | R | P | D | P | H | T | C | M | A | A | S |
| 101 | R | S | H | P | N | T | S | M | A | A | S |
| 102 | R | P | H | P | H | T | S | M | A | A | S |
| 103 | R | P | H | P | H | T | S | M | A | S | S |
| 104 | R | S | H | P | N | T | C | M | A | A | S |
| 105 | R | S | H | P | N | T | A | Y | A | A | S |
| 106 | R | S | H | P | A | T | C | M | A | A | S |
| 107 | R | P | H | P | H | T | C | M | A | A | S |
| 108 | R | P | D | P | A | T | C | M | A | A | S |
| 109 | R | S | H | G | N | T | C | M | A | A | S |
| 110 | R | S | H | P | H | R | C | M | A | A | S |
| 111 | R | P | H | P | H | T | S | Y | A | A | S |
| 112 | R | P | H | P | H | T | S | Y | A | S | S |
| 113 | R | P | H | G | A | T | A | Y | A | A | S |
| 114 | R | P | H | G | A | T | A | Y | A | S | S |
| 115 | R | P | H | G | N | T | S | M | K | A | S |
| 116 | R | P | H | G | N | T | S | M | A | A | S |
| 117 | R | P | H | G | N | T | A | M | K | A | S |
| 118 | R | P | H | G | H | T | A | M | A | A | S |
| 119 | R | P | H | G | A | T | A | M | K | A | S |
| 120 | R | S | D | G | R | R | P | Y | K | A | S |
| 121 | R | S | D | G | R | R | K | Y | I | A | S |
| 122 | R | S | D | G | R | R | K | Y | F | A | S |
| 123 | G | S | D | G | R | R | K | Y | K | A | S |
| 124 | R | S | D | G | R | R | K | K | K | A | S |
| 125 | D | S | D | G | R | R | K | Y | K | A | S |
| 126 | E | S | D | G | R | R | K | Y | K | A | S |
| 127 | R | Y | D | G | R | R | K | Y | K | A | S |
| 128 | R | S | D | G | R | R | K | P | K | A | S |
| 129 | R | S | D | G | R | R | K | Y | K | A | N |
| 130 | R | S | D | G | R | R | K | Y | K | A | C |

Full-Length Sequences of Wild-Type Porcine Trypsin and Selected Trypsin Variants:

```
Wild-type porcine trypsin, SEQ ID NO: 1:
IVGGYTCAAN SIPYQVSLNS GSHFCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DSCQGDSGGP

VVCNGQLQGI VSWGYGCAQK NKPGVYTKVC NYVNWIQQTI AAN

Variant S172A, SEQ ID NO: 2:
IVGGYTCAAN SIPYQVSLNS GSHFCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSWGYGCAQK NKPGVYTKVC NYVNWIQQTI AAN

Generic sequence of porcine trypsin with variable positions at amino
acid positions 24, 44, 56, 78, 99, 107, 125, 131, 170, 172 and
193; SEQ ID NO: 3:
IVGGYTCAAN SIPYQVSLNS GSHXCGGSLI NSQWVVSAAH CYKXRIQVRL GEHNIXVLEG

NEQFINAAKI ITHPNFNXNT LDNDIMLIKL SSPATLNSXV ATVSLPXSCA AAGTECLISG

WGNTXSSGSS XPSLLQCLKA PVLSDSSCKS SYPGQITGNM ICVGFLEGGX DXCQGDSGGP

VVCNGQLQGI VSXGYGCAQK NKPGVYTKVC NYVNWIQQTI AAN
```

```
SEQ ID NO: 4:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSAV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 5:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSLV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 6:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSFV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 7:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSWV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 8:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSGV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 9:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSYV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 10:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSTV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 11:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSNV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 12:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSDV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN
```

```
SEQ ID NO: 13:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSEV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 14:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSHV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 15:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTASSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 16:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTGSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 17:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTYSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 18:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTSSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 19:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTCSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 20:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTESSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 21:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTHSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN
```

```
SEQ ID NO: 22:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTLSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 23:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTQSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 24:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGY DACQGDSGGP

VVCNGQLQGI VSSGYGCAQK NKPGVYTKVC NYVNWIQQTI AAN

SEQ ID NO: 25:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 26:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGG DACQGDSGGP

VVCNGQLQGI VSSGYGCAQK NKPGVYTKVC NYVNWIQQTI AAN

SEQ ID NO: 27:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGN DACQGDSGGP

VVCNGQLQGI VSSGYGCAQK NKPGVYTKVC NYVNWIQQTI AAN

SEQ ID NO: 28:
IVGGYTCAAN SIPYQVSLNS GSHVCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 29:
IVGGYTCAAN SIPYQVSLNS GSHLCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 30:
IVGGYTCAAN SIPYQVSLNS GSHSCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN
```

```
SEQ ID NO: 31:
IVGGYTCAAN SIPYQVSLNS GSHQCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 32:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 33:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPTSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 34:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS APSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 35:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS LPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 36:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 37:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS TPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 38:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS CPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 39:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS NPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN
```

```
SEQ ID NO: 40:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS EPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 41:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS HPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 42:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 43:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DTCQGDSGGP

VVCNGQLQGI VSSGYGCAQK NKPGVYTKVC NYVNWIQQTI AAN

SEQ ID NO: 44:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DSCQGDSGGP

VVCNGQLQGI VSSGYGCAQK NKPGVYTKVC NYVNWIQQTI AAN

SEQ ID NO: 45:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DCCQGDSGGP

VVCNGQLQGI VSSGYGCAQK NKPGVYTKVC NYVNWIQQTI AAN

SEQ ID NO: 46:
IVGGYTCAAN SIPYQVSLNS GSHACGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 47:
IVGGYTCAAN SIPYQVSLNS GSHICGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 48:
IVGGYTCAAN SIPYQVSLNS GSHMCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN
```

```
SEQ ID NO: 49:
IVGGYTCAAN SIPYQVSLNS GSHTCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 50:
IVGGYTCAAN SIPYQVSLNS GSHNCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 51:
IVGGYTCAAN SIPYQVSLNS GSHKCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 52:
IVGGYTCAAN SIPYQVSLNS GSHRCGGSLI NSQWVVSAAH CYKLRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 53:
IVGGYTCAAN SIPYQVSLNS GSHRCGGSLI NSQWVVSAAH CYKPRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 54:
IVGGYTCAAN SIPYQVSLNS GSHRCGGSLI NSQWVVSAAH CYKSRIQVRL GEHNIAVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 55:
IVGGYTCAAN SIPYQVSLNS GSHRCGGSLI NSQWVVSAAH CYKSRIQVRL GEHNIWVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 56:
IVGGYTCAAN SIPYQVSLNS GSHRCGGSLI NSQWVVSAAH CYKSRIQVRL GEHNINVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 57:
IVGGYTCAAN SIPYQVSLNS GSHRCGGSLI NSQWVVSAAH CYKSRIQVRL GEHNIHVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN
```

```
SEQ ID NO: 58:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPPSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 59:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPGSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 60:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPSSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 61:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPDSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 62:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS VPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 63:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS IPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 64:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS WPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 65:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS GPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 66:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS SPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN
```

SEQ ID NO: 67:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS QPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 68:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS DPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 69:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSFGYGCAQK NKPGVYTKVC NYVNWIQQTI AAN

SEQ ID NO: 70:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSYGYGCAQK NKPGVYTKVC NYVNWIQQTI AAN

SEQ ID NO: 71:
IVGGYTCAAN SIPYQVSLNS GSHRCGGSLI NSQWVVSAAH CYKSRIQVRL GEHNIDVLEG

NEQFINAAKI ITHPNFNGNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSTGYGCAQK NKPGVYTKVC NYVNWIQQTI AAN

SEQ ID NO: 72:
IVGGYTCAAN SIPYQVSLNS GSHRCGGSLI NSQWVVSAAH CYKSRIQVRL GEHNIDVLEG

NEQFINAAKI ITHPNFNSNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 73:
IVGGYTCAAN SIPYQVSLNS GSHRCGGSLI NSQWVVSAAH CYKSRIQVRL GEHNIDVLEG

NEQFINAAKI ITHPNFNANT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 74:
IVGGYTCAAN SIPYQVSLNS GSHRCGGSLI NSQWVVSAAH CYKSRIQVRL GEHNIDVLEG

NEQFINAAKI ITHPNFNPNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 75:
IVGGYTCAAN SIPYQVSLNS GSHRCGGSLI NSQWVVSAAH CYKSRIQVRL GEHNIDVLEG

NEQFINAAKI ITHPNFNYNT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 76:
IVGGYTCAAN SIPYQVSLNS GSHRCGGSLI NSQWVVSAAH CYKSRIQVRL GEHNIDVLEG

NEQFINAAKI ITHPNFNENT LDNDIMLIKL SSPATLNSRV ATVSLPRSCA AAGTECLISG

WGNTKSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 77:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSHV ATVSLPTSCA AAGTECLISG

WGNTCSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 78:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSHV ATVSLPTSCA AAGTECLISG

WGNTCSSGSS YPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 79:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPRSCA AAGTECLISG

WGNTASSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 80:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSHV ATVSLPTSCA AAGTECLISG

WGNTSSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 81:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSHV ATVSLPTSCA AAGTECLISG

WGNTASSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 82:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPRSCA AAGTECLISG

WGNTCSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 83:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSNV ATVSLPTSCA AAGTECLISG

WGNTSSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 84:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSNV ATVSLPTSCA AAGTECLISG

WGNTSSSGSS MPSLLQCLKA PVLSDSSCKS SYPGQITGNM ICVGFLEGGK DSCQGDSGGP

VVCNGQLQGI VSSGYGCAQK NKPGVYTKVC NYVNWIQQTI AAN

```
SEQ ID NO: 85:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTCSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 86:
IVGGYTCAAN SIPYQVSLNS GSHRCGGSLI NSQWVVSAAH CYKPRIQVRL GEHNIDVLEG

NEQFINAAKI ITHPNFNPNT LDNDIMLIKL SSPATLNSAV ATVSLPTSCA AAGTECLISG

WGNTSSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 87:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTSSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 88:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTSSSGSS MPSLLQCLKA PVLSDSSCKS SYPGQITGNM ICVGFLEGGK DSCQGDSGGP

VVCNGQLQGI VSSGYGCAQK NKPGVYTKVC NYVNWIQQTI AAN

SEQ ID NO: 89:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTASSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 90:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTASSGSS MPSLLQCLKA PVLSDSSCKS SYPGQITGNM ICVGFLEGGK DSCQGDSGGP

VVCNGQLQGI VSSGYGCAQK NKPGVYTKVC NYVNWIQQTI AAN

SEQ ID NO: 91:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSAV ATVSLPTSCA AAGTECLISG

WGNTSSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 92:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSAV ATVSLPTSCA AAGTECLISG

WGNTCSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 93:
IVGGYTCAAN SIPYQVSLNS GSHRCGGSLI NSQWVVSAAH CYKSRIQVRL GEHNIDVLEG

NEQFINAAKI ITHPNFNPNT LDNDIMLIKL SSPATLNSNV ATVSLPTSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN
```

SEQ ID NO: 94:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSNV ATVSLPRSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 95:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPRSCA AAGTECLISG

WGNTSSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 96:
IVGGYTCAAN SIPYQVSLNS GSHRCGGSLI NSQWVVSAAH CYKPRIQVRL GEHNIDVLEG

NEQFINAAKI ITHPNFNPNT LDNDIMLIKL SSPATLNSHV ATVSLPRSCA AAGTECLISG

WGNTSSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 97:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSAV ATVSLPTSCA AAGTECLISG

WGNTASSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 98:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSAV ATVSLPTSCA AAGTECLISG

WGNTASSGSS MPSLLQCLKA PVLSDSSCKS SYPGQITGNM ICVGFLEGGA DSCQGDSGGP

VVCNGQLQGI VSSGYGCAQK NKPGVYTKVC NYVNWIQQTI AAN

SEQ ID NO: 99:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSNV ATVSLPTSCA AAGTECLISG

WGNTSSSGSS YPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 100:
IVGGYTCAAN SIPYQVSLNS GSHRCGGSLI NSQWVVSAAH CYKPRIQVRL GEHNIDVLEG

NEQFINAAKI ITHPNFNPNT LDNDIMLIKL SSPATLNSHV ATVSLPTSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 101:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSNV ATVSLPTSCA AAGTECLISG

WGNTSSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 102:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTSSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

```
SEQ ID NO: 103:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTSSSGSS MPSLLQCLKA PVLSDSSCKS SYPGQITGNM ICVGFLEGGA DSCQGDSGGP

VVCNGQLQGI VSSGYGCAQK NKPGVYTKVC NYVNWIQQTI AAN

SEQ ID NO: 104:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSNV ATVSLPTSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 105:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSNV ATVSLPTSCA AAGTECLISG

WGNTASSGSS YPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 106:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSAV ATVSLPTSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 107:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 108:
IVGGYTCAAN SIPYQVSLNS GSHRCGGSLI NSQWVVSAAH CYKPRIQVRL GEHNIDVLEG

NEQFINAAKI ITHPNFNPNT LDNDIMLIKL SSPATLNSAV ATVSLPTSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 109:
IVGGYTCAAN SIPYQVSLNS GSHRCGGSLI NSQWVVSAAH CYKSRIQVRL GEHNIHVLEG

NEQFINAAKI ITHPNFNGNT LDNDIMLIKL SSPATLNSNV ATVSLPTSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 110:
IVGGYTCAAN SIPYQVSLNS GSHRCGGSLI NSQWVVSAAH CYKSRIQVRL GEHNIHVLEG

NEQFINAAKI ITHPNFNPNT LDNDIMLIKL SSPATLNSHV ATVSLPRSCA AAGTECLISG

WGNTCSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 111:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AAGTECLISG

WGNTSSSGSS YPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN
```

-continued

SEQ ID NO: 112:
IVGGYTCAAN SIPYQVSLNS GSHRCGGSLI NSQWVVSAAH CYKPRIQVRL GEHNIHVLEG

NEQFINAAKI ITHPNFNPNT LDNDIMLIKL SSPATLNSHV ATVSLPTSCA AGTECLISG

WGNTSSSGSS YPSLLQCLKA PVLSDSSCKS SYPGQITGNM ICVGFLEGGA DSCQGDSGGP

VVCNGQLQGI VSSGYGCAQK NKPGVYTKVC NYVNWIQQTI AAN

SEQ ID NO: 113:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSAV ATVSLPTSCA AGTECLISG

WGNTASSGSS YPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 114:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSAV ATVSLPTSCA AGTECLISG

WGNTASSGSS YPSLLQCLKA PVLSDSSCKS SYPGQITGNM ICVGFLEGGA DSCQGDSGGP

VVCNGQLQGI VSSGYGCAQK NKPGVYTKVC NYVNWIQQTI AAN

SEQ ID NO: 115:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSNV ATVSLPTSCA AGTECLISG

WGNTSSSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 116:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSNV ATVSLPTSCA AGTECLISG

WGNTSSSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 117:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSNV ATVSLPTSCA AGTECLISG

WGNTASSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQ ID NO: 118:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSHV ATVSLPTSCA AGTECLISG

WGNTASSGSS MPSLLQCLKA PVLSDSSCKS SYPGQITGNM ICVGFLEGGA DACQGDSGGP

VVCNGQLQGI VSSGYGCAQK NKPGVYTKVC NYVNWIQQTI AAN

SEQ ID NO: 119:
IVGGYTCAAN SIPYQVSLNS GSHRCGGSLI NSQWVVSAAH CYKPRIQVRL GEHNIHVLEG

NEQFINAAKI ITHPNFNGNT LDNDIMLIKL SSPATLNSAV ATVSLPTSCA AGTECLISG

WGNTASSGSS MPSLLQCLKA PVLSDSSCKS SYPGQITGNM ICVGFLEGGK DACQGDSGGP

VVCNGQLQGI VSSGYGCAQK NKPGVYTKVC NYVNWIQQTI AAN

SEQUENCE LISTING

```
Sequence total quantity: 132
SEQ ID NO: 1           moltype = AA  length = 223
FEATURE                Location/Qualifiers
```

```
source                          1..223
                                mol_type = protein
                                organism = Sus scrofa
SEQUENCE: 1
IVGGYTCAAN SIPYQVSLNS GSHFCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DSCQGDSGGP   180
VVCNGQLQGI VSWGYGCAQK NKPGVYTKVC NYVNWIQQTI AAN                    223

SEQ ID NO: 2                    moltype = AA   length = 223
FEATURE                         Location/Qualifiers
REGION                          1..223
                                note = Porcine trypsin variant S172A
source                          1..223
                                mol_type = protein
                                organism = synthetic construct
SEQUENCE: 2
IVGGYTCAAN SIPYQVSLNS GSHFCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSWGYGCAQK NKPGVYTKVC NYVNWIQQTI AAN                    223

SEQ ID NO: 3                    moltype = AA   length = 223
FEATURE                         Location/Qualifiers
REGION                          1..223
                                note = Generic sequence of porcine trypsin with variable
                                 positions atamino acid positions 24, 44, 56, 78, 99, 107,
                                 125, 131, 170, 172and 193
source                          1..223
                                mol_type = protein
                                organism = synthetic construct
VAR_SEQ                         24
                                note = MISC_FEATURE - Xaa is selected from the group
                                 consisting of Ala, Asn, Arg, Gln,Ile, Leu, Lys, Met, Phe,
                                 Ser, Thr, and Val
VAR_SEQ                         44
                                note = MISC_FEATURE - Xaa is selected from the group
                                 consisting of Leu, Pro, and Ser
VAR_SEQ                         56
                                note = MISC_FEATURE - Xaa is selected from the group
                                 consisting of Ala, Asn, Asp, His,and Trp
VAR_SEQ                         78
                                note = MISC_FEATURE - Xaa is selected from the group
                                 consisting of Ala, Glu, Gly, Pro,Ser, and Tyr
VAR_SEQ                         99
                                note = MISC_FEATURE - Xaa is selected from the group
                                 consisting of Ala, Arg, Asn, Asp,Glu, Gly, His, Leu, Phe,
                                 Thr, Trp, and Tyr
VAR_SEQ                         107
                                note = MISC_FEATURE - Xaa is selected from the group
                                 consisting of Arg, Asp, Gly, Pro,Ser, and Thr
VAR_SEQ                         125
                                note = MISC_FEATURE - Xaa is selected from the group
                                 consisting of Ala, Cys, Gln, Glu,Gly, His, Leu, Lys, Ser,
                                 and Tyr
VAR_SEQ                         131
                                note = MISC_FEATURE - Xaa is selected from the group
                                 consisting of Ala, Asn, Asp, Cys,Gln; Glu, Gly, His, Ile,
                                 Leu, Met, Ser, Thr, Trp, Tyr, and Val
VAR_SEQ                         170
                                note = MISC_FEATURE - Xaa is selected from the group
                                 consisting of Ala, Asn, Gly, Lys,and Tyr
VAR_SEQ                         193
                                note = MISC_FEATURE - Xaa is selected from the group
                                 consisting of Phe, Ser, Thr, Trp,and Tyr
VAR_SEQ                         172
                                note = MISC_FEATURE - Xaa is selected from the group
                                 consisting of Ala, Cys, Ser, andThr
SEQUENCE: 3
IVGGYTCAAN SIPYQVSLNS GSHXCGGSLI NSQWVVSAAH CYKXRIQVRL GEHNIXVLEG    60
NEQFINAAKI ITHPNFNXNT LDNDIMLIKL SSPATLNSXV ATVSLPXSCA AAGTECLISG   120
WGNTXSSGSS XPSLLQCLKA PVLSDSSCKS SYPGQITGNM ICVGFLEGGX DXCQGDSGGP   180
VVCNGQLQGI VSXGYGCAQK NKPGVYTKVC NYVNWIQQTI AAN                    223

SEQ ID NO: 4                    moltype = AA   length = 223
FEATURE                         Location/Qualifiers
REGION                          1..223
                                note = Porcine trypsin variant no. 4
source                          1..223
```

```
                            mol_type = protein
                            organism = synthetic construct
SEQUENCE: 4
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSAV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 5               moltype = AA  length = 223
FEATURE                    Location/Qualifiers
REGION                     1..223
                            note = Porcine trypsin variant no. 5
source                     1..223
                            mol_type = protein
                            organism = synthetic construct
SEQUENCE: 5
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSLV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 6               moltype = AA  length = 223
FEATURE                    Location/Qualifiers
REGION                     1..223
                            note = Porcine trypsin variant no. 6
source                     1..223
                            mol_type = protein
                            organism = synthetic construct
SEQUENCE: 6
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSFV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 7               moltype = AA  length = 223
FEATURE                    Location/Qualifiers
REGION                     1..223
                            note = Porcine trypsin variant no. 7
source                     1..223
                            mol_type = protein
                            organism = synthetic construct
SEQUENCE: 7
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSWV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 8               moltype = AA  length = 223
FEATURE                    Location/Qualifiers
REGION                     1..223
                            note = Porcine trypsin variant no. 8
source                     1..223
                            mol_type = protein
                            organism = synthetic construct
SEQUENCE: 8
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSGV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 9               moltype = AA  length = 223
FEATURE                    Location/Qualifiers
REGION                     1..223
                            note = Porcine trypsin variant no. 9
source                     1..223
                            mol_type = protein
                            organism = synthetic construct
SEQUENCE: 9
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSYV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 10              moltype = AA  length = 223
FEATURE                    Location/Qualifiers
REGION                     1..223
                            note = Porcine trypsin variant no. 10
source                     1..223
                            mol_type = protein
```

```
                                        organism = synthetic construct
SEQUENCE: 10
IVGGYTCAAN SIPYQVSLNS GSHRCGGSLI NSQWVVSAAH CYKSRIQVRL GEHNIDVLEG      60
NEQFINAAKI ITHPNFNGNT LDNDIMLIKL SSPATLNSTV ATVSLPRSCA AAGTECLISG     120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                       223

SEQ ID NO: 11               moltype = AA  length = 223
FEATURE                     Location/Qualifiers
REGION                      1..223
                            note = Porcine trypsin variant no. 11
source                      1..223
                            mol_type = protein
                            organism = synthetic construct
SEQUENCE: 11
IVGGYTCAAN SIPYQVSLNS GSHRCGGSLI NSQWVVSAAH CYKSRIQVRL GEHNIDVLEG      60
NEQFINAAKI ITHPNFNGNT LDNDIMLIKL SSPATLNSNV ATVSLPRSCA AAGTECLISG     120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                       223

SEQ ID NO: 12               moltype = AA  length = 223
FEATURE                     Location/Qualifiers
REGION                      1..223
                            note = Porcine trypsin variant no. 12
source                      1..223
                            mol_type = protein
                            organism = synthetic construct
SEQUENCE: 12
IVGGYTCAAN SIPYQVSLNS GSHRCGGSLI NSQWVVSAAH CYKSRIQVRL GEHNIDVLEG      60
NEQFINAAKI ITHPNFNGNT LDNDIMLIKL SSPATLNSDV ATVSLPRSCA AAGTECLISG     120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                       223

SEQ ID NO: 13               moltype = AA  length = 223
FEATURE                     Location/Qualifiers
REGION                      1..223
                            note = Porcine trypsin variant no. 13
source                      1..223
                            mol_type = protein
                            organism = synthetic construct
SEQUENCE: 13
IVGGYTCAAN SIPYQVSLNS GSHRCGGSLI NSQWVVSAAH CYKSRIQVRL GEHNIDVLEG      60
NEQFINAAKI ITHPNFNGNT LDNDIMLIKL SSPATLNSEV ATVSLPRSCA AAGTECLISG     120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                       223

SEQ ID NO: 14               moltype = AA  length = 223
FEATURE                     Location/Qualifiers
REGION                      1..223
                            note = Porcine trypsin variant no. 14
source                      1..223
                            mol_type = protein
                            organism = synthetic construct
SEQUENCE: 14
IVGGYTCAAN SIPYQVSLNS GSHRCGGSLI NSQWVVSAAH CYKSRIQVRL GEHNIDVLEG      60
NEQFINAAKI ITHPNFNGNT LDNDIMLIKL SSPATLNSHV ATVSLPRSCA AAGTECLISG     120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                       223

SEQ ID NO: 15               moltype = AA  length = 223
FEATURE                     Location/Qualifiers
REGION                      1..223
                            note = Porcine trypsin variant no. 15
source                      1..223
                            mol_type = protein
                            organism = synthetic construct
SEQUENCE: 15
IVGGYTCAAN SIPYQVSLNS GSHRCGGSLI NSQWVVSAAH CYKSRIQVRL GEHNIDVLEG      60
NEQFINAAKI ITHPNFNGNT LDNDIMLIKL SSPATLNSRV ATVSLPRSCA AAGTECLISG     120
WGNTASSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                       223

SEQ ID NO: 16               moltype = AA  length = 223
FEATURE                     Location/Qualifiers
REGION                      1..223
                            note = Porcine trypsin variant no. 16
source                      1..223
                            mol_type = protein
                            organism = synthetic construct
```

```
SEQUENCE: 16
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTGSSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                   223

SEQ ID NO: 17           moltype = AA  length = 223
FEATURE                 Location/Qualifiers
REGION                  1..223
                        note = Porcine trypsin variant no. 17
source                  1..223
                        mol_type = protein
                        organism = synthetic construct
SEQUENCE: 17
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTYSSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                   223

SEQ ID NO: 18           moltype = AA  length = 223
FEATURE                 Location/Qualifiers
REGION                  1..223
                        note = Porcine trypsin variant no. 18
source                  1..223
                        mol_type = protein
                        organism = synthetic construct
SEQUENCE: 18
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTSSSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                   223

SEQ ID NO: 19           moltype = AA  length = 223
FEATURE                 Location/Qualifiers
REGION                  1..223
                        note = Porcine trypsin variant no. 19
source                  1..223
                        mol_type = protein
                        organism = synthetic construct
SEQUENCE: 19
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTCSSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                   223

SEQ ID NO: 20           moltype = AA  length = 223
FEATURE                 Location/Qualifiers
REGION                  1..223
                        note = Porcine trypsin variant no. 20
source                  1..223
                        mol_type = protein
                        organism = synthetic construct
SEQUENCE: 20
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTESSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                   223

SEQ ID NO: 21           moltype = AA  length = 223
FEATURE                 Location/Qualifiers
REGION                  1..223
                        note = Porcine trypsin variant no. 21
source                  1..223
                        mol_type = protein
                        organism = synthetic construct
SEQUENCE: 21
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTHSSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                   223

SEQ ID NO: 22           moltype = AA  length = 223
FEATURE                 Location/Qualifiers
REGION                  1..223
                        note = Porcine trypsin variant no. 22
source                  1..223
                        mol_type = protein
                        organism = synthetic construct
SEQUENCE: 22
```

```
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTLSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 23           moltype = AA  length = 223
FEATURE                 Location/Qualifiers
REGION                  1..223
                        note = Porcine trypsin variant no. 23
source                  1..223
                        mol_type = protein
                        organism = synthetic construct
SEQUENCE: 23
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTQSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 24           moltype = AA  length = 223
FEATURE                 Location/Qualifiers
REGION                  1..223
                        note = Porcine trypsin variant no. 24
source                  1..223
                        mol_type = protein
                        organism = synthetic construct
SEQUENCE: 24
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGY DACQGDSGGP   180
VVCNGQLQGI VSSGYGCAQK NKPGVYTKVC NYVNWIQQTI AAN                    223

SEQ ID NO: 25           moltype = AA  length = 223
FEATURE                 Location/Qualifiers
REGION                  1..223
                        note = Porcine trypsin variant no. 25
source                  1..223
                        mol_type = protein
                        organism = synthetic construct
SEQUENCE: 25
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 26           moltype = AA  length = 223
FEATURE                 Location/Qualifiers
REGION                  1..223
                        note = Porcine trypsin variant no. 26
source                  1..223
                        mol_type = protein
                        organism = synthetic construct
SEQUENCE: 26
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGG DACQGDSGGP   180
VVCNGQLQGI VSSGYGCAQK NKPGVYTKVC NYVNWIQQTI AAN                    223

SEQ ID NO: 27           moltype = AA  length = 223
FEATURE                 Location/Qualifiers
REGION                  1..223
                        note = Porcine trypsin variant no. 27
source                  1..223
                        mol_type = protein
                        organism = synthetic construct
SEQUENCE: 27
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGN DACQGDSGGP   180
VVCNGQLQGI VSSGYGCAQK NKPGVYTKVC NYVNWIQQTI AAN                    223

SEQ ID NO: 28           moltype = AA  length = 223
FEATURE                 Location/Qualifiers
REGION                  1..223
                        note = Porcine trypsin variant no. 28
source                  1..223
                        mol_type = protein
                        organism = synthetic construct
SEQUENCE: 28
IVGGYTCAAN SIPYQVSLNS GSHVCGGSLI NSQWVVSAAH CYKSRIQVRL GEHNIDVLEG    60
```

```
NEQFINAAKI ITHPNFNGNT LDNDIMLIKL SSPATLNSRV ATVSLPRSCA AAGTECLISG    120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                      223

SEQ ID NO: 29              moltype = AA   length = 223
FEATURE                    Location/Qualifiers
REGION                     1..223
                           note = Porcine trypsin variant no. 29
source                     1..223
                           mol_type = protein
                           organism = synthetic construct
SEQUENCE: 29
IVGGYTCAAN SIPYQVSLNS GSHLCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG    120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                      223

SEQ ID NO: 30              moltype = AA   length = 223
FEATURE                    Location/Qualifiers
REGION                     1..223
                           note = Porcine trypsin variant no. 30
source                     1..223
                           mol_type = protein
                           organism = synthetic construct
SEQUENCE: 30
IVGGYTCAAN SIPYQVSLNS GSHSCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG    120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                      223

SEQ ID NO: 31              moltype = AA   length = 223
FEATURE                    Location/Qualifiers
REGION                     1..223
                           note = Porcine trypsin variant no. 31
source                     1..223
                           mol_type = protein
                           organism = synthetic construct
SEQUENCE: 31
IVGGYTCAAN SIPYQVSLNS GSHQCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG    120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                      223

SEQ ID NO: 32              moltype = AA   length = 223
FEATURE                    Location/Qualifiers
REGION                     1..223
                           note = Porcine trypsin variant no. 32
source                     1..223
                           mol_type = protein
                           organism = synthetic construct
SEQUENCE: 32
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG    120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                      223

SEQ ID NO: 33              moltype = AA   length = 223
FEATURE                    Location/Qualifiers
REGION                     1..223
                           note = Porcine trypsin variant no. 33
source                     1..223
                           mol_type = protein
                           organism = synthetic construct
SEQUENCE: 33
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPTSCA AAGTECLISG    120
WGNTKSSGSS YPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                      223

SEQ ID NO: 34              moltype = AA   length = 223
FEATURE                    Location/Qualifiers
REGION                     1..223
                           note = Porcine trypsin variant no. 34
source                     1..223
                           mol_type = protein
                           organism = synthetic construct
SEQUENCE: 34
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG    120
```

```
WGNTKSSGSS APSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                      223

SEQ ID NO: 35            moltype = AA  length = 223
FEATURE                  Location/Qualifiers
REGION                   1..223
                         note = Porcine trypsin variant no. 35
source                   1..223
                         mol_type = protein
                         organism = synthetic construct
SEQUENCE: 35
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS LPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 36            moltype = AA  length = 223
FEATURE                  Location/Qualifiers
REGION                   1..223
                         note = Porcine trypsin variant no. 36
source                   1..223
                         mol_type = protein
                         organism = synthetic construct
SEQUENCE: 36
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS MPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 37            moltype = AA  length = 223
FEATURE                  Location/Qualifiers
REGION                   1..223
                         note = Porcine trypsin variant no. 37
source                   1..223
                         mol_type = protein
                         organism = synthetic construct
SEQUENCE: 37
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS TPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 38            moltype = AA  length = 223
FEATURE                  Location/Qualifiers
REGION                   1..223
                         note = Porcine trypsin variant no. 38
source                   1..223
                         mol_type = protein
                         organism = synthetic construct
SEQUENCE: 38
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS CPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 39            moltype = AA  length = 223
FEATURE                  Location/Qualifiers
REGION                   1..223
                         note = Porcine trypsin variant no. 39
source                   1..223
                         mol_type = protein
                         organism = synthetic construct
SEQUENCE: 39
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS NPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 40            moltype = AA  length = 223
FEATURE                  Location/Qualifiers
REGION                   1..223
                         note = Porcine trypsin variant no. 40
source                   1..223
                         mol_type = protein
                         organism = synthetic construct
SEQUENCE: 40
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS EPSLLQCLKA PVLSDSSCKS SYPGQITGNM ICVGFLEGGK DACQGDSGGP   180
```

```
VVCNGQLQGI VSSGYGCAQK NKPGVYTKVC NYVNWIQQTI AAN               223

SEQ ID NO: 41           moltype = AA  length = 223
FEATURE                 Location/Qualifiers
REGION                  1..223
                        note = Porcine trypsin variant no. 41
source                  1..223
                        mol_type = protein
                        organism = synthetic construct
SEQUENCE: 41
IVGGYTCAAN SIPYQVSLNS GSHRCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG 120
WGNTKSSGSS HPSLLQCLKA PVLSDSSCKS SYPGQITGNM ICVGFLEGGK DACQGDSGGP 180
VVCNGQLQGI VSSGYGCAQK NKPGVYTKVC NYVNWIQQTI AAN               223

SEQ ID NO: 42           moltype = AA  length = 223
FEATURE                 Location/Qualifiers
REGION                  1..223
                        note = Porcine trypsin variant no. 42
source                  1..223
                        mol_type = protein
                        organism = synthetic construct
SEQUENCE: 42
IVGGYTCAAN SIPYQVSLNS GSHRCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG 120
WGNTKSSGSS YPSLLQCLKA PVLSDSSCKS SYPGQITGNM ICVGFLEGGK DACQGDSGGP 180
VVCNGQLQGI VSSGYGCAQK NKPGVYTKVC NYVNWIQQTI AAN               223

SEQ ID NO: 43           moltype = AA  length = 223
FEATURE                 Location/Qualifiers
REGION                  1..223
                        note = Porcine trypsin variant no. 43
source                  1..223
                        mol_type = protein
                        organism = synthetic construct
SEQUENCE: 43
IVGGYTCAAN SIPYQVSLNS GSHRCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG 120
WGNTKSSGSS YPSLLQCLKA PVLSDSSCKS SYPGQITGNM ICVGFLEGGK DTCQGDSGGP 180
VVCNGQLQGI VSSGYGCAQK NKPGVYTKVC NYVNWIQQTI AAN               223

SEQ ID NO: 44           moltype = AA  length = 223
FEATURE                 Location/Qualifiers
REGION                  1..223
                        note = Porcine trypsin variant no. 44
source                  1..223
                        mol_type = protein
                        organism = synthetic construct
SEQUENCE: 44
IVGGYTCAAN SIPYQVSLNS GSHRCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG 120
WGNTKSSGSS YPSLLQCLKA PVLSDSSCKS SYPGQITGNM ICVGFLEGGK DSCQGDSGGP 180
VVCNGQLQGI VSSGYGCAQK NKPGVYTKVC NYVNWIQQTI AAN               223

SEQ ID NO: 45           moltype = AA  length = 223
FEATURE                 Location/Qualifiers
REGION                  1..223
                        note = Porcine trypsin variant no. 45
source                  1..223
                        mol_type = protein
                        organism = synthetic construct
SEQUENCE: 45
IVGGYTCAAN SIPYQVSLNS GSHRCGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG 120
WGNTKSSGSS YPSLLQCLKA PVLSDSSCKS SYPGQITGNM ICVGFLEGGK DCCQGDSGGP 180
VVCNGQLQGI VSSGYGCAQK NKPGVYTKVC NYVNWIQQTI AAN               223

SEQ ID NO: 46           moltype = AA  length = 223
FEATURE                 Location/Qualifiers
REGION                  1..223
                        note = Porcine trypsin variant no. 46
source                  1..223
                        mol_type = protein
                        organism = synthetic construct
SEQUENCE: 46
IVGGYTCAAN SIPYQVSLNS GSHACGGSLI NSQWVVSAAH CYKSRIQVRL GEHNIDVLEG  60
NEQFINAAKI ITHPNFNGNT LDNDIMLIKL SSPATLNSRV ATVSLPRSCA AAGTECLISG 120
WGNTKSSGSS YPSLLQCLKA PVLSDSSCKS SYPGQITGNM ICVGFLEGGK DACQGDSGGP 180
VVCNGQLQGI VSSGYGCAQK NKPGVYTKVC NYVNWIQQTI AAN               223
```

```
SEQ ID NO: 47            moltype = AA  length = 223
FEATURE                  Location/Qualifiers
REGION                   1..223
                         note = Porcine trypsin variant no. 47
source                   1..223
                         mol_type = protein
                         organism = synthetic construct
SEQUENCE: 47
IVGGYTCAAN SIPYQVSLNS GSHICGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 48            moltype = AA  length = 223
FEATURE                  Location/Qualifiers
REGION                   1..223
                         note = Porcine trypsin variant no. 48
source                   1..223
                         mol_type = protein
                         organism = synthetic construct
SEQUENCE: 48
IVGGYTCAAN SIPYQVSLNS GSHMCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 49            moltype = AA  length = 223
FEATURE                  Location/Qualifiers
REGION                   1..223
                         note = Porcine trypsin variant no. 49
source                   1..223
                         mol_type = protein
                         organism = synthetic construct
SEQUENCE: 49
IVGGYTCAAN SIPYQVSLNS GSHTCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 50            moltype = AA  length = 223
FEATURE                  Location/Qualifiers
REGION                   1..223
                         note = Porcine trypsin variant no. 50
source                   1..223
                         mol_type = protein
                         organism = synthetic construct
SEQUENCE: 50
IVGGYTCAAN SIPYQVSLNS GSHNCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 51            moltype = AA  length = 223
FEATURE                  Location/Qualifiers
REGION                   1..223
                         note = Porcine trypsin variant no. 51
source                   1..223
                         mol_type = protein
                         organism = synthetic construct
SEQUENCE: 51
IVGGYTCAAN SIPYQVSLNS GSHKCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 52            moltype = AA  length = 223
FEATURE                  Location/Qualifiers
REGION                   1..223
                         note = Porcine trypsin variant no. 52
source                   1..223
                         mol_type = protein
                         organism = synthetic construct
SEQUENCE: 52
IVGGYTCAAN SIPYQVSLNS GSHRCGGSLI NSQWVVSAAH CYKLRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223
```

```
SEQ ID NO: 53              moltype = AA  length = 223
FEATURE                    Location/Qualifiers
REGION                     1..223
                           note = Porcine trypsin variant no. 53
source                     1..223
                           mol_type = protein
                           organism = synthetic construct
SEQUENCE: 53
IVGGYTCAAN SIPYQVSLNS GSHRCGGSLI NSQWVVSAAH CYKPRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 54              moltype = AA  length = 223
FEATURE                    Location/Qualifiers
REGION                     1..223
                           note = Porcine trypsin variant no. 54
source                     1..223
                           mol_type = protein
                           organism = synthetic construct
SEQUENCE: 54
IVGGYTCAAN SIPYQVSLNS GSHRCGGSLI NSQWVVSAAH CYKSRIQVRL GEHNIAVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 55              moltype = AA  length = 223
FEATURE                    Location/Qualifiers
REGION                     1..223
                           note = Porcine trypsin variant no. 55
source                     1..223
                           mol_type = protein
                           organism = synthetic construct
SEQUENCE: 55
IVGGYTCAAN SIPYQVSLNS GSHRCGGSLI NSQWVVSAAH CYKSRIQVRL GEHNIWVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 56              moltype = AA  length = 223
FEATURE                    Location/Qualifiers
REGION                     1..223
                           note = Porcine trypsin variant no. 56
source                     1..223
                           mol_type = protein
                           organism = synthetic construct
SEQUENCE: 56
IVGGYTCAAN SIPYQVSLNS GSHRCGGSLI NSQWVVSAAH CYKSRIQVRL GEHNINVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 57              moltype = AA  length = 223
FEATURE                    Location/Qualifiers
REGION                     1..223
                           note = Porcine trypsin variant no. 57
source                     1..223
                           mol_type = protein
                           organism = synthetic construct
SEQUENCE: 57
IVGGYTCAAN SIPYQVSLNS GSHRCGGSLI NSQWVVSAAH CYKSRIQVRL GEHNIHVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 58              moltype = AA  length = 223
FEATURE                    Location/Qualifiers
REGION                     1..223
                           note = Porcine trypsin variant no. 58
source                     1..223
                           mol_type = protein
                           organism = synthetic construct
SEQUENCE: 58
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPPSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 59              moltype = AA  length = 223
```

```
FEATURE                 Location/Qualifiers
REGION                  1..223
                        note = Porcine trypsin variant no. 59
source                  1..223
                        mol_type = protein
                        organism = synthetic construct
SEQUENCE: 59
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPSSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 60           moltype = AA  length = 223
FEATURE                 Location/Qualifiers
REGION                  1..223
                        note = Porcine trypsin variant no. 60
source                  1..223
                        mol_type = protein
                        organism = synthetic construct
SEQUENCE: 60
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPSSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 61           moltype = AA  length = 223
FEATURE                 Location/Qualifiers
REGION                  1..223
                        note = Porcine trypsin variant no. 61
source                  1..223
                        mol_type = protein
                        organism = synthetic construct
SEQUENCE: 61
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPDSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 62           moltype = AA  length = 223
FEATURE                 Location/Qualifiers
REGION                  1..223
                        note = Porcine trypsin variant no. 62
source                  1..223
                        mol_type = protein
                        organism = synthetic construct
SEQUENCE: 62
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS VPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 63           moltype = AA  length = 223
FEATURE                 Location/Qualifiers
REGION                  1..223
                        note = Porcine trypsin variant no. 63
source                  1..223
                        mol_type = protein
                        organism = synthetic construct
SEQUENCE: 63
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS IPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 64           moltype = AA  length = 223
FEATURE                 Location/Qualifiers
REGION                  1..223
                        note = Porcine trypsin variant no. 64
source                  1..223
                        mol_type = protein
                        organism = synthetic construct
SEQUENCE: 64
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS WPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 65           moltype = AA  length = 223
FEATURE                 Location/Qualifiers
```

```
REGION                  1..223
                        note = Porcine trypsin variant no. 65
source                  1..223
                        mol_type = protein
                        organism = synthetic construct
SEQUENCE: 65
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS GPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 66           moltype = AA  length = 223
FEATURE                 Location/Qualifiers
REGION                  1..223
                        note = Porcine trypsin variant no. 66
source                  1..223
                        mol_type = protein
                        organism = synthetic construct
SEQUENCE: 66
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS SPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 67           moltype = AA  length = 223
FEATURE                 Location/Qualifiers
REGION                  1..223
                        note = Porcine trypsin variant no. 67
source                  1..223
                        mol_type = protein
                        organism = synthetic construct
SEQUENCE: 67
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS QPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 68           moltype = AA  length = 223
FEATURE                 Location/Qualifiers
REGION                  1..223
                        note = Porcine trypsin variant no. 68
source                  1..223
                        mol_type = protein
                        organism = synthetic construct
SEQUENCE: 68
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS DPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 69           moltype = AA  length = 223
FEATURE                 Location/Qualifiers
REGION                  1..223
                        note = Porcine trypsin variant no. 69
source                  1..223
                        mol_type = protein
                        organism = synthetic construct
SEQUENCE: 69
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSFGYGCAQK NKPGVYTKVC NYVNWIQQTI AAN                     223

SEQ ID NO: 70           moltype = AA  length = 223
FEATURE                 Location/Qualifiers
REGION                  1..223
                        note = Porcine trypsin variant no. 70
source                  1..223
                        mol_type = protein
                        organism = synthetic construct
SEQUENCE: 70
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSYGYGCAQK NKPGVYTKVC NYVNWIQQTI AAN                     223

SEQ ID NO: 71           moltype = AA  length = 223
FEATURE                 Location/Qualifiers
REGION                  1..223
```

```
                        note = Porcine trypsin variant no. 71
source                  1..223
                        mol_type = protein
                        organism = synthetic construct
SEQUENCE: 71
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSTGYGCAQK NKPGVYTKVC NYVNWIQQTI AAN                    223

SEQ ID NO: 72           moltype = AA   length = 223
FEATURE                 Location/Qualifiers
REGION                  1..223
                        note = Porcine trypsin variant no. 72
source                  1..223
                        mol_type = protein
                        organism = synthetic construct
SEQUENCE: 72
IVGGYTCAAN SIPYQVSLNS GSHRCGGSLI NSQWVVSAAH CYKSRIQVRL GEHNIDVLEG    60
NEQFINAAKI ITHPNFNSNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 73           moltype = AA   length = 223
FEATURE                 Location/Qualifiers
REGION                  1..223
                        note = Porcine trypsin variant no. 73
source                  1..223
                        mol_type = protein
                        organism = synthetic construct
SEQUENCE: 73
IVGGYTCAAN SIPYQVSLNS GSHRCGGSLI NSQWVVSAAH CYKSRIQVRL GEHNIDVLEG    60
NEQFINAAKI ITHPNFNANT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 74           moltype = AA   length = 223
FEATURE                 Location/Qualifiers
REGION                  1..223
                        note = Porcine trypsin variant no. 74
source                  1..223
                        mol_type = protein
                        organism = synthetic construct
SEQUENCE: 74
IVGGYTCAAN SIPYQVSLNS GSHRCGGSLI NSQWVVSAAH CYKSRIQVRL GEHNIDVLEG    60
NEQFINAAKI ITHPNFNPNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 75           moltype = AA   length = 223
FEATURE                 Location/Qualifiers
REGION                  1..223
                        note = Porcine trypsin variant no. 75
source                  1..223
                        mol_type = protein
                        organism = synthetic construct
SEQUENCE: 75
IVGGYTCAAN SIPYQVSLNS GSHRCGGSLI NSQWVVSAAH CYKSRIQVRL GEHNIDVLEG    60
NEQFINAAKI ITHPNFNYNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 76           moltype = AA   length = 223
FEATURE                 Location/Qualifiers
REGION                  1..223
                        note = Porcine trypsin variant no. 76
source                  1..223
                        mol_type = protein
                        organism = synthetic construct
SEQUENCE: 76
IVGGYTCAAN SIPYQVSLNS GSHRCGGSLI NSQWVVSAAH CYKSRIQVRL GEHNIDVLEG    60
NEQFINAAKI ITHPNFNENT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 77           moltype = AA   length = 223
FEATURE                 Location/Qualifiers
REGION                  1..223
                        note = Porcine trypsin variant no. 77
```

```
source                  1..223
                        mol_type = protein
                        organism = synthetic construct
SEQUENCE: 77
IVGGYTCAAN SIPYQVSLNS GSHRCGGSLI NSQWVVSAAH CYKPRIQVRL GEHNIHVLEG    60
NEQFINAAKI ITHPNFNGNT LDNDIMLIKL SSPATLNSHV ATVSLPTSCA AAGTECLISG   120
WGNTCSSGSS MPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 78           moltype = AA   length = 223
FEATURE                 Location/Qualifiers
REGION                  1..223
                        note = Porcine trypsin variant no. 78
source                  1..223
                        mol_type = protein
                        organism = synthetic construct
SEQUENCE: 78
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSHV ATVSLPTSCA AAGTECLISG   120
WGNTCSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 79           moltype = AA   length = 223
FEATURE                 Location/Qualifiers
REGION                  1..223
                        note = Porcine trypsin variant no. 79
source                  1..223
                        mol_type = protein
                        organism = synthetic construct
SEQUENCE: 79
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSHV ATVSLPRSCA AAGTECLISG   120
WGNTASSGSS MPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 80           moltype = AA   length = 223
FEATURE                 Location/Qualifiers
REGION                  1..223
                        note = Porcine trypsin variant no. 80
source                  1..223
                        mol_type = protein
                        organism = synthetic construct
SEQUENCE: 80
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSHV ATVSLPTSCA AAGTECLISG   120
WGNTSSSGSS MPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 81           moltype = AA   length = 223
FEATURE                 Location/Qualifiers
REGION                  1..223
                        note = Porcine trypsin variant no. 81
source                  1..223
                        mol_type = protein
                        organism = synthetic construct
SEQUENCE: 81
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSHV ATVSLPTSCA AAGTECLISG   120
WGNTASSGSS MPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 82           moltype = AA   length = 223
FEATURE                 Location/Qualifiers
REGION                  1..223
                        note = Porcine trypsin variant no. 82
source                  1..223
                        mol_type = protein
                        organism = synthetic construct
SEQUENCE: 82
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSHV ATVSLPRSCA AAGTECLISG   120
WGNTCSSGSS MPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                     223

SEQ ID NO: 83           moltype = AA   length = 223
FEATURE                 Location/Qualifiers
REGION                  1..223
                        note = Porcine trypsin variant no. 83
source                  1..223
```

```
                        mol_type = protein
                        organism = synthetic construct
SEQUENCE: 83
IVGGYTCAAN SIPYQVSLNS GSHRCGGSLI NSQWVVSAAH CYKPRIQVRL GEHNIHVLEG     60
NEQFINAAKI ITHPNFNPNT LDNDIMLIKL SSPATLNSNV ATVSLPTSCA AAGTECLISG    120
WGNTSSSGSS MPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                     223

SEQ ID NO: 84           moltype = AA  length = 223
FEATURE                 Location/Qualifiers
REGION                  1..223
                        note = Porcine trypsin variant no. 84
source                  1..223
                        mol_type = protein
                        organism = synthetic construct
SEQUENCE: 84
IVGGYTCAAN SIPYQVSLNS GSHRCGGSLI NSQWVVSAAH CYKPRIQVRL GEHNIHVLEG     60
NEQFINAAKI ITHPNFNPNT LDNDIMLIKL SSPATLNSNV ATVSLPTSCA AAGTECLISG    120
WGNTSSSGSS MPSLLQCLKA PVLSDSSCKS SYPGQITGNM ICVGFLEGGK DSCQGDSGGP    180
VVCNGQLQGI VSSGYGCAQK NKPGVYTKVC NYVNWIQQTI AAN                     223

SEQ ID NO: 85           moltype = AA  length = 223
FEATURE                 Location/Qualifiers
REGION                  1..223
                        note = Porcine trypsin variant no. 85
source                  1..223
                        mol_type = protein
                        organism = synthetic construct
SEQUENCE: 85
IVGGYTCAAN SIPYQVSLNS GSHRCGGSLI NSQWVVSAAH CYKPRIQVRL GEHNIHVLEG     60
NEQFINAAKI ITHPNFNPNT LDNDIMLIKL SSPATLNSHV ATVSLPTSCA AAGTECLISG    120
WGNTCSSGSS MPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                     223

SEQ ID NO: 86           moltype = AA  length = 223
FEATURE                 Location/Qualifiers
REGION                  1..223
                        note = Porcine trypsin variant no. 86
source                  1..223
                        mol_type = protein
                        organism = synthetic construct
SEQUENCE: 86
IVGGYTCAAN SIPYQVSLNS GSHRCGGSLI NSQWVVSAAH CYKPRIQVRL GEHNIDVLEG     60
NEQFINAAKI ITHPNFNPNT LDNDIMLIKL SSPATLNSAV ATVSLPTSCA AAGTECLISG    120
WGNTSSSGSS MPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                     223

SEQ ID NO: 87           moltype = AA  length = 223
FEATURE                 Location/Qualifiers
REGION                  1..223
                        note = Porcine trypsin variant no. 87
source                  1..223
                        mol_type = protein
                        organism = synthetic construct
SEQUENCE: 87
IVGGYTCAAN SIPYQVSLNS GSHRCGGSLI NSQWVVSAAH CYKPRIQVRL GEHNIHVLEG     60
NEQFINAAKI ITHPNFNPNT LDNDIMLIKL SSPATLNSHV ATVSLPTSCA AAGTECLISG    120
WGNTSSSGSS MPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                     223

SEQ ID NO: 88           moltype = AA  length = 223
FEATURE                 Location/Qualifiers
REGION                  1..223
                        note = Porcine trypsin variant no. 88
source                  1..223
                        mol_type = protein
                        organism = synthetic construct
SEQUENCE: 88
IVGGYTCAAN SIPYQVSLNS GSHRCGGSLI NSQWVVSAAH CYKPRIQVRL GEHNIHVLEG     60
NEQFINAAKI ITHPNFNPNT LDNDIMLIKL SSPATLNSHV ATVSLPTSCA AAGTECLISG    120
WGNTSSSGSS MPSLLQCLKA PVLSDSSCKS SYPGQITGNM ICVGFLEGGK DSCQGDSGGP    180
VVCNGQLQGI VSSGYGCAQK NKPGVYTKVC NYVNWIQQTI AAN                     223

SEQ ID NO: 89           moltype = AA  length = 223
FEATURE                 Location/Qualifiers
REGION                  1..223
                        note = Porcine trypsin variant no. 89
source                  1..223
                        mol_type = protein
```

```
                        organism = synthetic construct
SEQUENCE: 89
IVGGYTCAAN SIPYQVSLNS GSHRCGGSLI NSQWVVSAAH CYKPRIQVRL GEHNIHVLEG       60
NEQFINAAKI ITHPNFNPNT LDNDIMLIKL SSPATLNSHV ATVSLPTSCA AAGTECLISG      120
WGNTASSGSS MPSLLQCLKA PVLSDSSCKS SYPGQITGNM ICVGFLEGGK DACQGDSGGP      180
VVCNGQLQGI VSSGYGCAQK NKPGVYTKVC NYVNWIQQTI AAN                       223

SEQ ID NO: 90           moltype = AA  length = 223
FEATURE                 Location/Qualifiers
REGION                  1..223
                        note = Porcine trypsin variant no. 90
source                  1..223
                        mol_type = protein
                        organism = synthetic construct
SEQUENCE: 90
IVGGYTCAAN SIPYQVSLNS GSHRCGGSLI NSQWVVSAAH CYKPRIQVRL GEHNIHVLEG       60
NEQFINAAKI ITHPNFNPNT LDNDIMLIKL SSPATLNSHV ATVSLPTSCA AAGTECLISG      120
WGNTASSGSS MPSLLQCLKA PVLSDSSCKS SYPGQITGNM ICVGFLEGGK DSCQGDSGGP      180
VVCNGQLQGI VSSGYGCAQK NKPGVYTKVC NYVNWIQQTI AAN                       223

SEQ ID NO: 91           moltype = AA  length = 223
FEATURE                 Location/Qualifiers
REGION                  1..223
                        note = Porcine trypsin variant no. 91
source                  1..223
                        mol_type = protein
                        organism = synthetic construct
SEQUENCE: 91
IVGGYTCAAN SIPYQVSLNS GSHRCGGSLI NSQWVVSAAH CYKPRIQVRL GEHNIHVLEG       60
NEQFINAAKI ITHPNFNPNT LDNDIMLIKL SSPATLNSAV ATVSLPTSCA AAGTECLISG      120
WGNTSSSGSS MPSLLQCLKA PVLSDSSCKS SYPGQITGNM ICVGFLEGGK DACQGDSGGP      180
VVCNGQLQGI VSSGYGCAQK NKPGVYTKVC NYVNWIQQTI AAN                       223

SEQ ID NO: 92           moltype = AA  length = 223
FEATURE                 Location/Qualifiers
REGION                  1..223
                        note = Porcine trypsin variant no. 92
source                  1..223
                        mol_type = protein
                        organism = synthetic construct
SEQUENCE: 92
IVGGYTCAAN SIPYQVSLNS GSHRCGGSLI NSQWVVSAAH CYKPRIQVRL GEHNIHVLEG       60
NEQFINAAKI ITHPNFNPNT LDNDIMLIKL SSPATLNSAV ATVSLPTSCA AAGTECLISG      120
WGNTCSSGSS MPSLLQCLKA PVLSDSSCKS SYPGQITGNM ICVGFLEGGK DACQGDSGGP      180
VVCNGQLQGI VSSGYGCAQK NKPGVYTKVC NYVNWIQQTI AAN                       223

SEQ ID NO: 93           moltype = AA  length = 223
FEATURE                 Location/Qualifiers
REGION                  1..223
                        note = Porcine trypsin variant no. 93
source                  1..223
                        mol_type = protein
                        organism = synthetic construct
SEQUENCE: 93
IVGGYTCAAN SIPYQVSLNS GSHRCGGSLI NSQWVVSAAH CYKSRIQVRL GEHNIDVLEG       60
NEQFINAAKI ITHPNFNPNT LDNDIMLIKL SSPATLNSNV ATVSLPTSCA AAGTECLISG      120
WGNTCSSGSS MPSLLQCLKA PVLSDSSCKS SYPGQITGNM ICVGFLEGGA DACQGDSGGP      180
VVCNGQLQGI VSSGYGCAQK NKPGVYTKVC NYVNWIQQTI AAN                       223

SEQ ID NO: 94           moltype = AA  length = 223
FEATURE                 Location/Qualifiers
REGION                  1..223
                        note = Porcine trypsin variant no. 94
source                  1..223
                        mol_type = protein
                        organism = synthetic construct
SEQUENCE: 94
IVGGYTCAAN SIPYQVSLNS GSHRCGGSLI NSQWVVSAAH CYKPRIQVRL GEHNIHVLEG       60
NEQFINAAKI ITHPNFNGNT LDNDIMLIKL SSPATLNSNV ATVSLPRSCA AAGTECLISG      120
WGNTCSSGSS MPSLLQCLKA PVLSDSSCKS SYPGQITGNM ICVGFLEGGA DACQGDSGGP      180
VVCNGQLQGI VSSGYGCAQK NKPGVYTKVC NYVNWIQQTI AAN                       223

SEQ ID NO: 95           moltype = AA  length = 223
FEATURE                 Location/Qualifiers
REGION                  1..223
                        note = Porcine trypsin variant no. 95
source                  1..223
                        mol_type = protein
                        organism = synthetic construct
```

```
SEQUENCE: 95
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSHV ATVSLPRSCA AAGTECLISG   120
WGNTSSSGSS MPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 96           moltype = AA   length = 223
FEATURE                 Location/Qualifiers
REGION                  1..223
                        note = Porcine trypsin variant no. 96
source                  1..223
                        mol_type = protein
                        organism = synthetic construct
SEQUENCE: 96
IVGGYTCAAN SIPYQVSLNS GSHRCGGSLI NSQWVVSAAH CYKPRIQVRL GEHNIDVLEG    60
NEQFINAAKI ITHPNFNPNT LDNDIMLIKL SSPATLNSHV ATVSLPRSCA AAGTECLISG   120
WGNTSSSGSS MPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 97           moltype = AA   length = 223
FEATURE                 Location/Qualifiers
REGION                  1..223
                        note = Porcine trypsin variant no. 97
source                  1..223
                        mol_type = protein
                        organism = synthetic construct
SEQUENCE: 97
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSAV ATVSLPTSCA AAGTECLISG   120
WGNTASSGSS MPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 98           moltype = AA   length = 223
FEATURE                 Location/Qualifiers
REGION                  1..223
                        note = Porcine trypsin variant no. 98
source                  1..223
                        mol_type = protein
                        organism = synthetic construct
SEQUENCE: 98
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSAV ATVSLPTSCA AAGTECLISG   120
WGNTASSGSS MPSLLQCLKA PVLSDSSCKS SYPGQITGNM ICVGFLEGGA DSCQGDSGGP   180
VVCNGQLQGI VSSGYGCAQK NKPGVYTKVC NYVNWIQQTI AAN                    223

SEQ ID NO: 99           moltype = AA   length = 223
FEATURE                 Location/Qualifiers
REGION                  1..223
                        note = Porcine trypsin variant no. 99
source                  1..223
                        mol_type = protein
                        organism = synthetic construct
SEQUENCE: 99
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSNV ATVSLPTSCA AAGTECLISG   120
WGNTSSSGSS YPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 100          moltype = AA   length = 223
FEATURE                 Location/Qualifiers
REGION                  1..223
                        note = Porcine trypsin variant no. 100
source                  1..223
                        mol_type = protein
                        organism = synthetic construct
SEQUENCE: 100
IVGGYTCAAN SIPYQVSLNS GSHRCGGSLI NSQWVVSAAH CYKPRIQVRL GEHNIDVLEG    60
NEQFINAAKI ITHPNFNPNT LDNDIMLIKL SSPATLNSHV ATVSLPTSCA AAGTECLISG   120
WGNTCSSGSS MPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 101          moltype = AA   length = 223
FEATURE                 Location/Qualifiers
REGION                  1..223
                        note = Porcine trypsin variant no. 101
source                  1..223
                        mol_type = protein
                        organism = synthetic construct
SEQUENCE: 101
```

```
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSNV ATVSLPTSCA AAGTECLISG   120
WGNTSSSGSS MPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 102          moltype = AA   length = 223
FEATURE                 Location/Qualifiers
REGION                  1..223
                        note = Porcine trypsin variant no. 102
source                  1..223
                        mol_type = protein
                        organism = synthetic construct
SEQUENCE: 102
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSHV ATVSLPTSCA AAGTECLISG   120
WGNTSSSGSS MPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 103          moltype = AA   length = 223
FEATURE                 Location/Qualifiers
REGION                  1..223
                        note = Porcine trypsin variant no. 103
source                  1..223
                        mol_type = protein
                        organism = synthetic construct
SEQUENCE: 103
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSHV ATVSLPTSCA AAGTECLISG   120
WGNTSSSGSS MPSLLQCLKA PVLSDSSCKS SYPGQITGNM ICVGFLEGGA DSCQGDSGGP   180
VVCNGQLQGI VSSGYGCAQK NKPGVYTKVC NYVNWIQQTI AAN                    223

SEQ ID NO: 104          moltype = AA   length = 223
FEATURE                 Location/Qualifiers
REGION                  1..223
                        note = Porcine trypsin variant no. 104
source                  1..223
                        mol_type = protein
                        organism = synthetic construct
SEQUENCE: 104
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSNV ATVSLPTSCA AAGTECLISG   120
WGNTCSSGSS MPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 105          moltype = AA   length = 223
FEATURE                 Location/Qualifiers
REGION                  1..223
                        note = Porcine trypsin variant no. 105
source                  1..223
                        mol_type = protein
                        organism = synthetic construct
SEQUENCE: 105
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSNV ATVSLPTSCA AAGTECLISG   120
WGNTASSGSS YPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 106          moltype = AA   length = 223
FEATURE                 Location/Qualifiers
REGION                  1..223
                        note = Porcine trypsin variant no. 106
source                  1..223
                        mol_type = protein
                        organism = synthetic construct
SEQUENCE: 106
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSAV ATVSLPTSCA AAGTECLISG   120
WGNTCSSGSS MPSLLQCLKA PVLSDSSCKS SYPGQITGNM ICVGFLEGGA DACQGDSGGP   180
VVCNGQLQGI VSSGYGCAQK NKPGVYTKVC NYVNWIQQTI AAN                    223

SEQ ID NO: 107          moltype = AA   length = 223
FEATURE                 Location/Qualifiers
REGION                  1..223
                        note = Porcine trypsin variant no. 107
source                  1..223
                        mol_type = protein
                        organism = synthetic construct
SEQUENCE: 107
IVGGYTCAAN SIPYQVSLNS GSHRCGGSLI NSQWVVSAAH CYKPRIQVRL GEHNIHVLEG    60
```

```
NEQFINAAKI ITHPNFNPNT LDNDIMLIKL SSPATLNSHV ATVSLPTSCA AAGTECLISG    120
WGNTCSSGSS MPSLLQCLKA PVLSDSSCKS SYPGQITGNM ICVGFLEGGA DACQGDSGGP    180
VVCNGQLQGI VSSGYGCAQK NKPGVYTKVC NYVNWIQQTI AAN                      223

SEQ ID NO: 108          moltype = AA  length = 223
FEATURE                 Location/Qualifiers
REGION                  1..223
                        note = Porcine trypsin variant no. 108
source                  1..223
                        mol_type = protein
                        organism = synthetic construct
SEQUENCE: 108
IVGGYTCAAN SIPYQVSLNS GSHRCGGSLI NSQWVVSAAH CYKPRIQVRL GEHNIDVLEG    60
NEQFINAAKI ITHPNFNPNT LDNDIMLIKL SSPATLNSAV ATVSLPTSCA AAGTECLISG    120
WGNTCSSGSS MPSLLQCLKA PVLSDSSCKS SYPGQITGNM ICVGFLEGGA DACQGDSGGP    180
VVCNGQLQGI VSSGYGCAQK NKPGVYTKVC NYVNWIQQTI AAN                      223

SEQ ID NO: 109          moltype = AA  length = 223
FEATURE                 Location/Qualifiers
REGION                  1..223
                        note = Porcine trypsin variant no. 109
source                  1..223
                        mol_type = protein
                        organism = synthetic construct
SEQUENCE: 109
IVGGYTCAAN SIPYQVSLNS GSHRCGGSLI NSQWVVSAAH CYKSRIQVRL GEHNIHVLEG    60
NEQFINAAKI ITHPNFNGNT LDNDIMLIKL SSPATLNSNV ATVSLPTSCA AAGTECLISG    120
WGNTCSSGSS MPSLLQCLKA PVLSDSSCKS SYPGQITGNM ICVGFLEGGA DACQGDSGGP    180
VVCNGQLQGI VSSGYGCAQK NKPGVYTKVC NYVNWIQQTI AAN                      223

SEQ ID NO: 110          moltype = AA  length = 223
FEATURE                 Location/Qualifiers
REGION                  1..223
                        note = Porcine trypsin variant no. 110
source                  1..223
                        mol_type = protein
                        organism = synthetic construct
SEQUENCE: 110
IVGGYTCAAN SIPYQVSLNS GSHRCGGSLI NSQWVVSAAH CYKSRIQVRL GEHNIHVLEG    60
NEQFINAAKI ITHPNFNPNT LDNDIMLIKL SSPATLNSHV ATVSLPRSCA AAGTECLISG    120
WGNTCSSGSS MPSLLQCLKA PVLSDSSCKS SYPGQITGNM ICVGFLEGGA DACQGDSGGP    180
VVCNGQLQGI VSSGYGCAQK NKPGVYTKVC NYVNWIQQTI AAN                      223

SEQ ID NO: 111          moltype = AA  length = 223
FEATURE                 Location/Qualifiers
REGION                  1..223
                        note = Porcine trypsin variant no. 111
source                  1..223
                        mol_type = protein
                        organism = synthetic construct
SEQUENCE: 111
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSHV ATVSLPTSCA AAGTECLISG    120
WGNTSSSGSS YPSLLQCLKA PVLSDSSCKS SYPGQITGNM ICVGFLEGGA DACQGDSGGP    180
VVCNGQLQGI VSSGYGCAQK NKPGVYTKVC NYVNWIQQTI AAN                      223

SEQ ID NO: 112          moltype = AA  length = 223
FEATURE                 Location/Qualifiers
REGION                  1..223
                        note = Porcine trypsin variant no. 112
source                  1..223
                        mol_type = protein
                        organism = synthetic construct
SEQUENCE: 112
IVGGYTCAAN SIPYQVSLNS GSHRCGGSLI NSQWVVSAAH CYKPRIQVRL GEHNIHVLEG    60
NEQFINAAKI ITHPNFNPNT LDNDIMLIKL SSPATLNSHV ATVSLPTSCA AAGTECLISG    120
WGNTSSSGSS YPSLLQCLKA PVLSDSSCKS SYPGQITGNM ICVGFLEGGA DSCQGDSGGP    180
VVCNGQLQGI VSSGYGCAQK NKPGVYTKVC NYVNWIQQTI AAN                      223

SEQ ID NO: 113          moltype = AA  length = 223
FEATURE                 Location/Qualifiers
REGION                  1..223
                        note = Porcine trypsin variant no. 113
source                  1..223
                        mol_type = protein
                        organism = synthetic construct
SEQUENCE: 113
IVGGYTCAAN SIPYQVSLNS GSHRCGGSLI NSQWVVSAAH CYKPRIQVRL GEHNIHVLEG    60
NEQFINAAKI ITHPNFNGNT LDNDIMLIKL SSPATLNSAV ATVSLPTSCA AAGTECLISG    120
```

```
WGNTASSGSS YPSLLQCLKA PVLSDSSCKS SYPGQITGNM ICVGFLEGGA DACQGDSGGP    180
VVCNGQLQGI VSSGYGCAQK NKPGVYTKVC NYVNWIQQTI AAN                     223

SEQ ID NO: 114          moltype = AA  length = 223
FEATURE                 Location/Qualifiers
REGION                  1..223
                        note = Porcine trypsin variant no. 114
source                  1..223
                        mol_type = protein
                        organism = synthetic construct
SEQUENCE: 114
IVGGYTCAAN SIPYQVSLNS GSHRCGGSLI NSQWVVSAAH CYKPRIQVRL GEHNIHVLEG    60
NEQFINAAKI ITHPNFNGNT LDNDIMLIKL SSPATLNSAV ATVSLPTSCA AAGTECLISG    120
WGNTASSGSS YPSLLQCLKA PVLSDSSCKS SYPGQITGNM ICVGFLEGGA DSCQGDSGGP    180
VVCNGQLQGI VSSGYGCAQK NKPGVYTKVC NYVNWIQQTI AAN                     223

SEQ ID NO: 115          moltype = AA  length = 223
FEATURE                 Location/Qualifiers
REGION                  1..223
                        note = Porcine trypsin variant no. 115
source                  1..223
                        mol_type = protein
                        organism = synthetic construct
SEQUENCE: 115
IVGGYTCAAN SIPYQVSLNS GSHRCGGSLI NSQWVVSAAH CYKPRIQVRL GEHNIHVLEG    60
NEQFINAAKI ITHPNFNGNT LDNDIMLIKL SSPATLNSNV ATVSLPTSCA AAGTECLISG    120
WGNTSSSGSS MPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                     223

SEQ ID NO: 116          moltype = AA  length = 223
FEATURE                 Location/Qualifiers
REGION                  1..223
                        note = Porcine trypsin variant no. 116
source                  1..223
                        mol_type = protein
                        organism = synthetic construct
SEQUENCE: 116
IVGGYTCAAN SIPYQVSLNS GSHRCGGSLI NSQWVVSAAH CYKPRIQVRL GEHNIHVLEG    60
NEQFINAAKI ITHPNFNGNT LDNDIMLIKL SSPATLNSNV ATVSLPTSCA AAGTECLISG    120
WGNTSSSGSS MPSLLQCLKA PVLSDSSCKS SYPGQITGNM ICVGFLEGGA DACQGDSGGP    180
VVCNGQLQGI VSSGYGCAQK NKPGVYTKVC NYVNWIQQTI AAN                     223

SEQ ID NO: 117          moltype = AA  length = 223
FEATURE                 Location/Qualifiers
REGION                  1..223
                        note = Porcine trypsin variant no. 117
source                  1..223
                        mol_type = protein
                        organism = synthetic construct
SEQUENCE: 117
IVGGYTCAAN SIPYQVSLNS GSHRCGGSLI NSQWVVSAAH CYKPRIQVRL GEHNIHVLEG    60
NEQFINAAKI ITHPNFNGNT LDNDIMLIKL SSPATLNSNV ATVSLPTSCA AAGTECLISG    120
WGNTASSGSS MPSLLQCLKA PVLSDSSCKS SYPGQITGNM ICVGFLEGGK DACQGDSGGP    180
VVCNGQLQGI VSSGYGCAQK NKPGVYTKVC NYVNWIQQTI AAN                     223

SEQ ID NO: 118          moltype = AA  length = 223
FEATURE                 Location/Qualifiers
REGION                  1..223
                        note = Porcine trypsin variant no. 118
source                  1..223
                        mol_type = protein
                        organism = synthetic construct
SEQUENCE: 118
IVGGYTCAAN SIPYQVSLNS GSHRCGGSLI NSQWVVSAAH CYKPRIQVRL GEHNIHVLEG    60
NEQFINAAKI ITHPNFNGNT LDNDIMLIKL SSPATLNSHV ATVSLPTSCA AAGTECLISG    120
WGNTASSGSS MPSLLQCLKA PVLSDSSCKS SYPGQITGNM ICVGFLEGGA DACQGDSGGP    180
VVCNGQLQGI VSSGYGCAQK NKPGVYTKVC NYVNWIQQTI AAN                     223

SEQ ID NO: 119          moltype = AA  length = 223
FEATURE                 Location/Qualifiers
REGION                  1..223
                        note = Porcine trypsin variant no. 119
source                  1..223
                        mol_type = protein
                        organism = synthetic construct
SEQUENCE: 119
IVGGYTCAAN SIPYQVSLNS GSHRCGGSLI NSQWVVSAAH CYKPRIQVRL GEHNIHVLEG    60
NEQFINAAKI ITHPNFNGNT LDNDIMLIKL SSPATLNSAV ATVSLPTSCA AAGTECLISG    120
WGNTASSGSS MPSLLQCLKA PVLSDSSCKS SYPGQITGNM ICVGFLEGGK DACQGDSGGP    180
```

```
VVCNGQLQGI VSSGYGCAQK NKPGVYTKVC NYVNWIQQTI AAN              223

SEQ ID NO: 120          moltype = AA   length = 223
FEATURE                 Location/Qualifiers
REGION                  1..223
                        note = Porcine trypsin variant no. 120
source                  1..223
                        mol_type = protein
                        organism = synthetic construct
SEQUENCE: 120
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTPSSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                    223

SEQ ID NO: 121          moltype = AA   length = 223
FEATURE                 Location/Qualifiers
REGION                  1..223
                        note = Porcine trypsin variant no. 121
source                  1..223
                        mol_type = protein
                        organism = synthetic construct
SEQUENCE: 121
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTKSSGSS YPSLLQCLKA PVLSDSSCKS SYPGQITGNM ICVGFLEGGI DACQGDSGGP  180
VVCNGQLQGI VSSGYGCAQK NKPGVYTKVC NYVNWIQQTI AAN                    223

SEQ ID NO: 122          moltype = AA   length = 223
FEATURE                 Location/Qualifiers
REGION                  1..223
                        note = Porcine trypsin variant no. 122
source                  1..223
                        mol_type = protein
                        organism = synthetic construct
SEQUENCE: 122
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTKSSGSS YPSLLQCLKA PVLSDSSCKS SYPGQITGNM ICVGFLEGGF DACQGDSGGP  180
VVCNGQLQGI VSSGYGCAQK NKPGVYTKVC NYVNWIQQTI AAN                    223

SEQ ID NO: 123          moltype = AA   length = 223
FEATURE                 Location/Qualifiers
REGION                  1..223
                        note = Porcine trypsin variant no. 123
source                  1..223
                        mol_type = protein
                        organism = synthetic construct
SEQUENCE: 123
IVGGYTCAAN SIPYQVSLNS GSHGCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTKSSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                    223

SEQ ID NO: 124          moltype = AA   length = 223
FEATURE                 Location/Qualifiers
REGION                  1..223
                        note = Porcine trypsin variant no. 124
source                  1..223
                        mol_type = protein
                        organism = synthetic construct
SEQUENCE: 124
IVGGYTCAAN SIPYQVSLNS GSHRCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTKSSGSS KPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                    223

SEQ ID NO: 125          moltype = AA   length = 223
FEATURE                 Location/Qualifiers
REGION                  1..223
                        note = Porcine trypsin variant no. 125
source                  1..223
                        mol_type = protein
                        organism = synthetic construct
SEQUENCE: 125
IVGGYTCAAN SIPYQVSLNS GSHDCGGSLI NSQWVVSAAH CYKSRIQVRL GEHNIDVLEG   60
NEQFINAAKI ITHPNFNGNT LDNDIMLIKL SSPATLNSRV ATVSLPRSCA AAGTECLISG  120
WGNTKSSGSS YPSLLQCLKA PVLSDSSCKS SYPGQITGNM ICVGFLEGGK DACQGDSGGP  180
VVCNGQLQGI VSSGYGCAQK NKPGVYTKVC NYVNWIQQTI AAN                    223
```

```
SEQ ID NO: 126            moltype = AA   length = 223
FEATURE                   Location/Qualifiers
REGION                    1..223
                          note = Porcine trypsin variant no. 126
source                    1..223
                          mol_type = protein
                          organism = synthetic construct
SEQUENCE: 126
IVGGYTCAAN SIPYQVSLNS GSHECGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 127            moltype = AA   length = 223
FEATURE                   Location/Qualifiers
REGION                    1..223
                          note = Porcine trypsin variant no. 127
source                    1..223
                          mol_type = protein
                          organism = synthetic construct
SEQUENCE: 127
IVGGYTCAAN SIPYQVSLNS GSHRCGGSLI NSQWVVSAAH CYKYRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 128            moltype = AA   length = 223
FEATURE                   Location/Qualifiers
REGION                    1..223
                          note = Porcine trypsin variant no. 128
source                    1..223
                          mol_type = protein
                          organism = synthetic construct
SEQUENCE: 128
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS PPSLLQCLKA PVLSDSSCKS SYPGQITGNM ICVGFLEGGK DACQGDSGGP   180
VVCNGQLQGI VSSGYGCAQK NKPGVYTKVC NYVNWIQQTI AAN                    223

SEQ ID NO: 129            moltype = AA   length = 223
FEATURE                   Location/Qualifiers
REGION                    1..223
                          note = Porcine trypsin variant no. 129
source                    1..223
                          mol_type = protein
                          organism = synthetic construct
SEQUENCE: 129
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSNGYGCAQK NKPGVYTKVC NYVNWIQQTI AAN                    223

SEQ ID NO: 130            moltype = AA   length = 223
FEATURE                   Location/Qualifiers
REGION                    1..223
                          note = Porcine trypsin variant no. 130
source                    1..223
                          mol_type = protein
                          organism = synthetic construct
SEQUENCE: 130
IVGGYTCAAN SIPYQVSLNS GSHRCGGSLI NSQWVVSAAH CYKSRIQVRL GEHNIDVLEG    60
NEQFINAAKI ITHPNFNGNT LDNDIMLIKL SSPATLNSRV ATVSLPRSCA AAGTECLISG   120
WGNTKSSGSS YPSLLQCLKA PVLSDSSCKS SYPGQITGNM ICVGFLEGGK DACQGDSGGP   180
VVCNGQLQGI VSCGYGCAQK NKPGVYTKVC NYVNWIQQTI AAN                    223

SEQ ID NO: 131            moltype = AA   length = 6
FEATURE                   Location/Qualifiers
REGION                    1..6
                          note = general formula of cleavable peptide
PEPTIDE                   1
PEPTIDE                   6
source                    1..6
                          mol_type = protein
                          organism = synthetic construct
SEQUENCE: 131
AKTRRB                                                               6

SEQ ID NO: 132            moltype = AA   length = 5
```

```
FEATURE         Location/Qualifiers
REGION          1..5
                note = general formula of cleavable peptide
PEPTIDE         1
source          1..5
                mol_type = protein
                organism = synthetic construct
SEQUENCE: 132
AKTRR                                                         5
```

The invention claimed is:

1. A method for the production of human insulin, an insulin analogue or a derivative of insulin, the method comprising using a variant of porcine trypsin, wherein the variant of porcine trypsin comprises:
 an amino acid sequence that has at least 91% sequence identity to SEQ ID NO: 1,
 wherein said amino acid sequence differs from SEQ ID NO: 1 at least by one or more amino acid substitutions at one or more positions corresponding to F24, S44, D56, G78, Y131, S172 and W193 of native porcine trypsin according to SEQ ID NO: 1,
 with the proviso that said amino acid sequence is not native porcine trypsin according to SEQ ID NO: 1; and
 with the proviso that said amino acid sequence is not porcine variant trypsin S172A according to SEQ ID NO: 2.

2. The method of claim 1, wherein the insulin analogue is selected from the group consisting of insulin aspart, insulin lispro, insulin glulisine, and insulin glargine.

3. The method of claim 1, wherein the amino acid at the position corresponding to F24 is substituted by an amino acid selected from the group consisting of Ala, Asn, Arg, Gln, Ile, Leu, Lys, Met, Ser, Thr, and Val.

4. The method of claim 1, wherein the amino acid at the position corresponding to S44 is substituted by an amino acid selected from the group consisting of Leu and Pro.

5. The method of claim 1, wherein the amino acid at the position corresponding to D56 is substituted by an amino acid selected from the group consisting of Ala, Asn, His, and Trp.

6. The method of claim 1, wherein the amino acid at the position corresponding to G78 is substituted by an amino acid selected from the group consisting of Ala, Glu; Pro, Ser, and Tyr.

7. The method of claim 1, wherein the amino acid at the position corresponding to Y131 is substituted by an amino acid selected from the group consisting of Ala, Asn, Asp, Cys, Gln; Glu, Gly, His, Ile, Leu, Met, Ser, Thr, Trp, and Val.

8. The method of claim 1, wherein the amino acid at the position corresponding to S172 is substituted by an amino acid selected from the group consisting of Ala, Cys, and Thr.

9. The method of claim 1, wherein the amino acid at the position corresponding to W193 is substituted by an amino acid selected from the group consisting of Phe, Ser, Thr, and Tyr.

10. The method of claim 1, wherein said amino acid sequence additionally differs from SEQ ID NO: 1 at least by one or more amino acid substitutions at one or more positions corresponding to R99, R107, K125, and K170 of native porcine trypsin according to SEQ ID NO: 1.

11. The method of claim 10, wherein the amino acid at the position corresponding to R99 is substituted by an amino acid selected from the group consisting of Ala, Asn, Asp, Glu, Gly, His, Leu, Phe, Thr, Trp, and Tyr.

12. The method of claim 10, wherein the amino acid at the position corresponding to R107 is substituted by an amino acid selected from the group consisting of Asp, Gly, Pro, Ser, and Thr.

13. The method of claim 10, wherein the amino acid at the position corresponding to K125 is substituted by an amino acid selected from the group consisting of Ala, Cys, Gln, Glu, Gly, His, Leu, Ser, and Tyr.

14. The method of claim 10, wherein the amino acid at the position corresponding to K170 is substituted by an amino acid selected from the group consisting of Ala, Asn, Gly, and Tyr.

15. The method of claim 1, wherein said amino acid sequence is SEQ ID NO: 3, wherein Xaa24 is an amino acid selected from the group consisting of Ala, Asn, Arg, Gln, Ile, Leu, Lys, Met, Phe, Ser, Thr, and Val, with the proviso that SEQ ID NO: 3 is not the sequence of SEQ ID NOs: 1 and 2.

16. The method of claim 1, wherein said amino acid sequence is SEQ ID NO: 3, wherein
 Xaa44 is an amino acid selected from the group consisting of Leu, Pro, and Ser;
 Xaa56 is an amino acid selected from the group consisting of Ala, Asn, Asp, His, and Trp;
 Xaa78 is an amino acid selected from the group consisting of Ala, Glu, Gly, Pro, Ser, and Tyr;
 Xaa99 is an amino acid selected from the group consisting of Ala, Arg, Asn, Asp, Glu, Gly, His, Leu, Phe, Thr, Trp, and Tyr;
 Xaa107 is an amino acid selected from the group consisting of Arg, Asp, Gly, Pro, Ser, and Thr;
 Xaa125 is an amino acid selected from the group consisting of Ala, Cys, Gln, Glu, Gly, His, Leu, Lys, Ser, and Tyr;
 Xaa131 is an amino acid selected from the group consisting of Ala, Asn, Asp, Cys, Gln; Glu, Gly, His, Ile, Leu, Met, Ser, Thr, Trp, Tyr, and Val;
 Xaa170 is an amino acid selected from the group consisting of Ala, Asn, Gly, Lys, and Tyr;
 Xaa172 is an amino acid selected from the group consisting of Ala, Cys, Ser, and Thr; and/or
 Xaa193 is an amino acid selected from the group consisting of Phe, Ser, Thr, Trp, and Tyr; with the proviso that SEQ ID NO: 3 is not the sequence of SEQ ID NOs: 1 and 2.

17. The method of claim 1, wherein said amino acid sequence is selected from the group consisting of SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 53, SEQ ID NO: 54, SEQ ID NO: 55, SEQ ID NO: 56, SEQ ID NO: 57, SEQ ID NO: 58, SEQ ID NO: 59, SEQ ID NO:, 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, and SEQ ID NO: 119.

18. The method of claim 1, wherein said variant is capable of cleaving a peptide with the general formula A-Lys-Thr-Arg-Arg-B according to SEQ ID NO: 131 to yield a cleavage product of the general formula A-Lys-Thr-Arg-Arg according to SEQ ID NO: 132 in a yield of at least 80%,
  wherein A is an amino acid sequence consisting of one or more amino acids; and
  wherein B is an amino acid sequence consisting of one or more amino acids.

19. The method of claim 1, wherein the variant exhibits an increased selectivity for the cleavage of a pre-pro-human insulin, pre-pro-insulin glargine, pre-pro-insulin lispro, pre-pro-insulin aspart, or pre-pro-insulin glulisine at a position C-terminally to position B32-Arg as compared to porcine variant trypsin S172A according to SEQ ID NO: 2.

20. The method of claim 1, further comprising contacting a pre-pro human insulin, pre-pro insulin analogue, or a derivative of a pre-pro insulin with the variant of porcine trypsin.

\* \* \* \* \*